United States Patent
Hayakawa et al.

[11] Patent Number: 5,961,843
[45] Date of Patent: Oct. 5, 1999

[54] ANTIMICROBIAL SOLID MATERIAL, PROCESS FOR PRODUCING THE SAME, AND METHOD OF UTILIZING THE SAME

[75] Inventors: Makoto Hayakawa; Toshiya Watanabe; Tamon Kimura; Mitsuyoshi Kanno; Keiichiro Norimoto, all of Kitakyusyu, Japan

[73] Assignee: Toto Ltd., Fukuoka, Japan

[21] Appl. No.: 08/809,450

[22] PCT Filed: Oct. 5, 1995

[86] PCT No.: PCT/JP95/02044

§ 371 Date: Apr. 3, 1997

§ 102(e) Date: Apr. 3, 1997

[87] PCT Pub. No.: WO96/10917

PCT Pub. Date: Apr. 18, 1996

[30] Foreign Application Priority Data

| Oct. 5, 1994 | [JP] | Japan | 6-278243 |
| Jan. 18, 1995 | [JP] | Japan | 7-37502 |
| Jan. 19, 1995 | [JP] | Japan | 7-38957 |
| Mar. 1, 1995 | [JP] | Japan | 7-80647 |
| Apr. 10, 1995 | [JP] | Japan | 7-120352 |

[51] Int. Cl.⁶ ......................... A01N 59/16; A01N 59/20; C02F 1/50

[52] U.S. Cl. ......................... 210/748; 210/764; 210/192; 210/501; 422/6; 422/24; 424/421; 424/490; 424/618; 424/630; 424/641

[58] Field of Search .......................... 422/6, 24; 210/668, 210/764, 748, 197, 501; 424/405, 421, 489, 490, 617–619, 630, 641

[56] References Cited

U.S. PATENT DOCUMENTS

| 4,552,752 | 11/1985 | Amick | 210/764 |
| 4,933,178 | 6/1990 | Capelli | 424/405 |
| 5,256,390 | 10/1993 | Hu | 424/618 |
| 5,296,238 | 3/1994 | Sugiura et al. | 424/617 |
| 5,415,836 | 5/1995 | Yoshioka et al. | 422/6 |
| 5,476,660 | 12/1995 | Somasundaran et al. | 424/489 |
| 5,698,210 | 12/1997 | Levy | 424/405 |
| 5,709,870 | 1/1998 | Yoshimura | 424/405 |
| 5,785,845 | 7/1998 | Colaiano | 210/192 |

FOREIGN PATENT DOCUMENTS

| 2-19308 | 1/1990 | Japan . |
| 3-7201 | 1/1991 | Japan . |
| 3-83905 | 4/1991 | Japan . |
| 3-255010 | 11/1991 | Japan . |
| 4-243908 | 9/1992 | Japan . |
| 5-4816 | 1/1993 | Japan . |
| 5-70869 | 3/1993 | Japan . |
| 5-229911 | 9/1993 | Japan . |
| 6-65012 | 3/1994 | Japan . |
| 6-298532 | 10/1994 | Japan . |

*Primary Examiner*—Thomas G. Wyse
*Attorney, Agent, or Firm*—Jones, Day, Reavis & Pogue

[57] ABSTRACT

An antimicrobial solid material having a satisfactory antimicrobial activity for a long term against sewage in any form of circulating, static and flowing waters or contacting portions thereof and a utilizing method thereof are provided. An antimicrobial solid material as one embodiment of the present invention comprises both of an antimicrobial metal ion and an antimicrobial metal in a metal state. In general, it is believed that antimicrobial metal ions have a potent antimicrobial effect when they exist in a liquid to be treated with a certain concentration or more, but they are rapidly released and exhausted so that their antimicrobial effects cannot last long. On the other hand, it is believed that the antimicrobial metal in a metal state does not have a prompt effect, but exhibits a certain bacteriostatic and fungistatic effect continuously for a long term. Therefore, the antimicrobial solid material containing both of the antimicrobial metal ions and the antimicrobial metal in a metal state thereof has both of a potent initial antimicrobial activity and an enduring bacteriostatic and fungistatic activity.

34 Claims, 10 Drawing Sheets

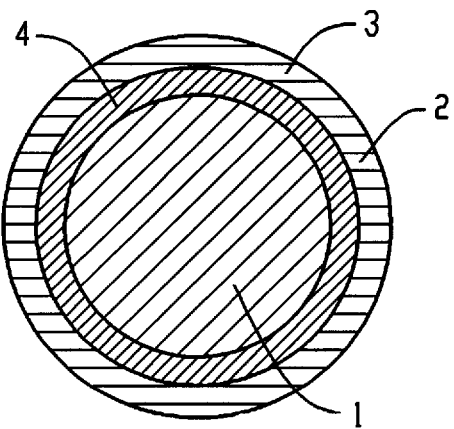
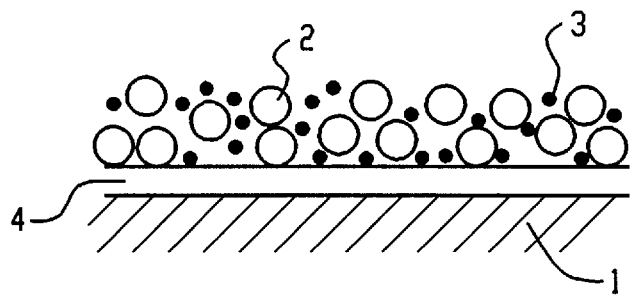
Fig. 5(a)     Fig. 5(b)
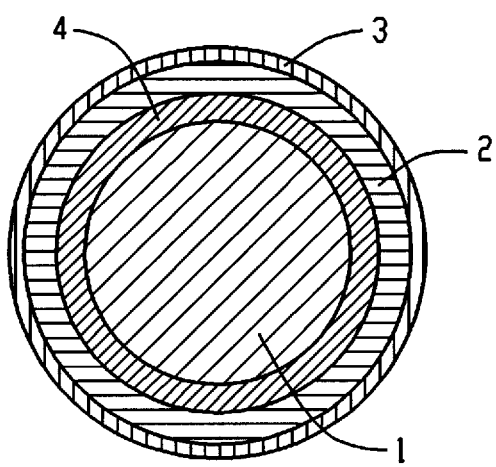
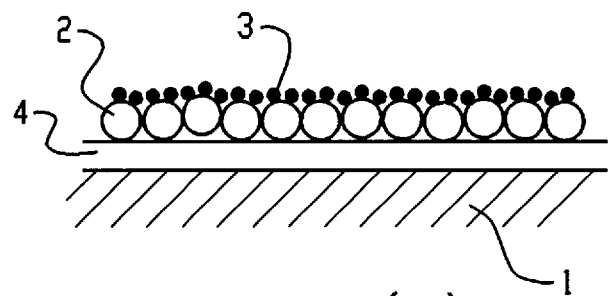
Fig. 6(a)     Fig. 6(b)

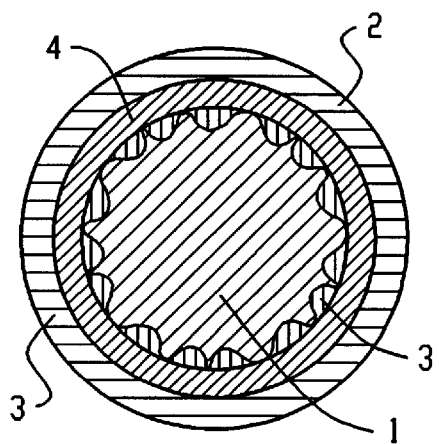
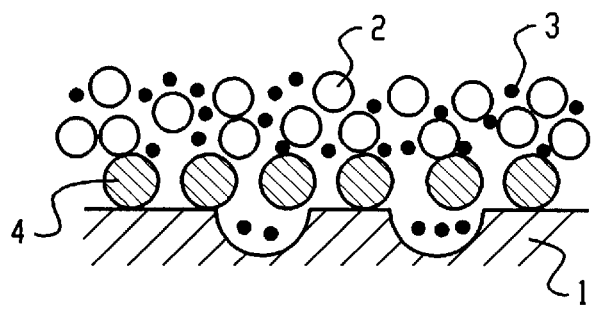
Fig. 7(a)          Fig. 7(b)
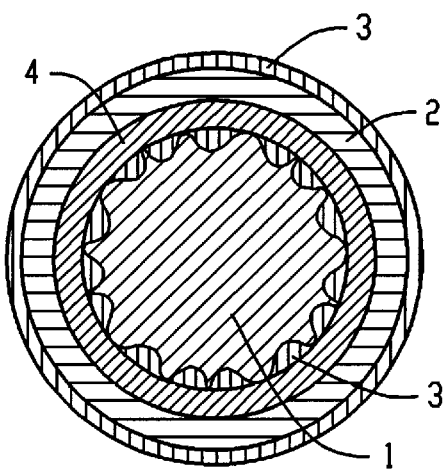
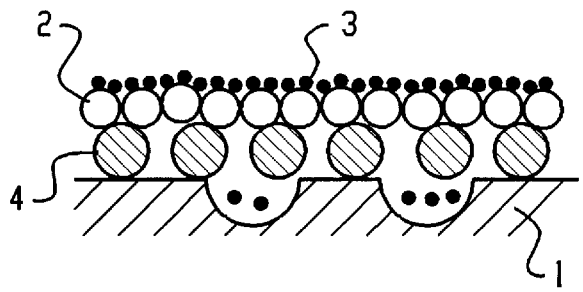
Fig. 8(a)          Fig. 8(b)

ANTIMICROBIAL SOLID MATERIAL, PROCESS FOR PRODUCING THE SAME, AND METHOD OF UTILIZING THE SAME

TECHNICAL FIELD TO WHICH THE INVENTION BELONGS

The present invention relates to an antimicrobial solid material which is suitably used for sterilization (killing bacteria and fungi) of a liquid such as sewage, and the like, or antimicrobial use at a surface of parts contacting with sewage, process for producing the same, and the like.

PRIOR ART

Liquids such as sewage, and the like, having high needs of antimicrobial action and forms of contacting portions with such liquids can be classified to the following three types.
(1) Circulating water type: circulating water in a circulating installments such as a bubble bath, an artificial fall, a pool, a cooling tower, and the like, and contacting portions thereof.
(2) Collected water type: a medical instrument such as a urine collecting bag, a chest drain bag, and the like, water kept for a long time such as a water tank, a bath water, and the like, and contacting portions thereof.
(3) Flowing water type: washing water of a stool, flowing water occurred at a washing space such as a kitchen, a sink, a bathroom, and the like, and contacting portions thereof.

In recent years, in the field of antimicrobial techniques, inorganic antimicrobial agents mainly comprising silver ions as antimicrobial materials have been attracted to attention since it is excellent in safety, heat resistance and persistency as compared with organic antimicrobial agents. And, as a specific form of the antimicrobial agent, a structure in which a silver ion is carried on a porous ceramic is generally employed since it can effectively show its antimicrobial characteristics of silver ions as well as it has a form which can be easily used. As the porous ceramic which is a carrier, zeolite (Japanese Laid-Open Patent Publication No. 255010/1991), layered silicate (Japanese Laid-Open Patent Publication No. 19308/1990), calcium phosphate (Japanese Laid-Open Patent Publication No. 243908/1992), zirconium phosphate (Japanese Laid-Open Patent Publication No. 83905/1991), aluminum phosphate (Japanese Laid-Open Patent Publication No. 229911/1993), soluble glass (Japanese Laid-Open Patent Publication No. 7201/1991), titanium oxide (Japanese Laid-Open Patent Publication No. 65012/1994, Japanese Laid-Open Patent Publication No. 816/1993, Japanese Laid-Open Patent Publication No. 9853/1994), and the like, have been utilized.

In order to show the antimicrobial activity of silver sufficiently, it has been described that it is desired to keep silver in an ion state enriched in reactivity (J. Antibact. Antifung. Agents, Vol. 22, No. 3 (1994)). In the above proposal, it is devised to hold silver to a carrier preferably as a silver ion or to gradually release silver from a carrier as a silver ion. However, it has been known that a metal state silver has a certain degree of a bactericidal effect ("inorganic chemistry (the first volume)", Sangyo Tosho, Tokyo, Japan (1959)).

PROBLEMS TO BE SOLVED BY THE INVENTION

However, in either of the method of supporting silver ions to a carrier, the method of gradually releasing in a liquid to be treated as silver ions as described above, or the method of adopting powder of metal silver directly to a liquid to be treated which has been conventionally carried out, it was not sufficient to keep antimicrobial action in either of the above mentioned three forms (circulating water, collected water, flowing water) for a long period.

As a method for gradually releasing silver ions in a system, there is a method as described in Japanese Laid-Open Patent Publication No. 19308/1990. In Japanese Laid-Open Patent Publication No. 19308/1990, there is disclosed an antimicrobial silicate having a film forming property in which at least part of metals which are exchangeable ion contained in a layered silicate is replaced with at least one kind of metal selected from silver, copper and zinc, specifically silver montmorillonite. The silver montmorillonite releases silver ions so that it shows certainly excellent antimicrobial activity at an initial stage. However, when the object is flowing water, collected water, and the like, or when a liquid which contains a large amount of alkali metal ions such as Na, K, and the like, like urine is an object, it loses its effect relatively within a short period.

Here, the reason why the antimicrobial activity is lost within a relatively short period when the object is circulating water or collected water is that the metal ion easily reacts with a chlorine ion, and the like, existing in the liquid to be treated and thus, the metal ion easily reacts to a silver salt or a complex ion having less antimicrobial activity. Also, the metal ion is likely consumed by binding to a cell membrane which generally has a negative charge.

On the other hand, the reason why the antimicrobial activity is lost within a relatively short period when the object is the liquid containing a large amount of an alkali metal ion such as Na, K, and the like, like urine is considered that, in an ion exchange method, an antimicrobial metal ion is fixed so that exchange of an alkali metal ion with the antimicrobial metal ion occurs at once and dissolution of the antimicrobial metal ion is too increased.

When silver powder in metal state is used, an antimicrobial activity was insufficient at the contacting portion when the object is flowing water or in the case of flowing water or collected water existing a plenty amount of nutrient source such as bouillon, and the like.

In this case, the reason why the antimicrobial effect is insufficient when the object is flowing water can be considered as mentioned below. That is, silver powder in the metal state is weak in absolute antimicrobial activity than that of silver ions so that, for conducting a sufficient antimicrobial action, it is necessary to react silver with an antimicrobial objective material for a relatively long time. However, when the object is flowing water, water and the antimicrobial agent do not contact with each other for such a long time so that it can be considered that the antimicrobial effect is limited to be insufficient. On the other hand, the reason why the antimicrobial effect is insufficient when the object is flowing water, and the like, existing a plenty amount of nutrient source and the number of initial bacteria is relatively large is considered that antimicrobial activity of silver powder is not so potent to sufficiently inhibit rapid growth of bacteria.

An object of the present invention is, in view of the above problems, to provide an antimicrobial solid material which has sufficient antimicrobial activity to any form of sewage of circulating water, collected water and flowing water and contacting portion thereof for a long period, process for producing the same, and method of utilizing the same.

MEANS FOR SOLVING THE PROBLEMS

An antimicrobial solid material which is one embodiment of the present invention is characterised in that both of an antimicrobial metal ion and antimicrobial metal in a metal state are contained.

In general, the antimicrobial metal ion has potent antimicrobial effect when it exist in a liquid to be treated in an amount of a certain concentration or more, but it is rapidly released in the liquid to be treated and consumed so that it is said that its antimicrobial effect does not last long. On the other hand, the antimicrobial metal in the state of metal has no immediate effect but it is said that it shows a certain degree of antimicrobial effects for a long period continuously. Therefore, the antimicrobial solid material containing both of the antimicrobial metal ion and antimicrobial metal in a metal state has both of initial strong antimicrobial activity and bacteriostatic and fungiostatic activity which continue for a long period.

EMBODIMENT FOR PRACTICING THE PRESENT INVENTION

An antimicrobial solid material which is the other embodiment of the present intention is characterised in that both of an antimicrobial metal ion and an antimicrobial metal in metal state are supported to a substrate. As one of preferred substrates, there may be mentioned porous ceramics. By impregnating a solution containing metal ions into porous ceramics, a large amount of metal ions can be supported to the substrate.

An antimicrobial solid material which is one of the other embodiments of the present intention is characterised in that the solid material has a substrate, an antimicrobial metal ion layer supported to the substrate, and an antimicrobial metal layer in a metal state fixed on said antimicrobial metal ion layer and through which said antimicrobial metal ion is permeable. Such an antimicrobial solid material shows both of an antimicrobial effect due to the antimicrobial metal in a metal state existing at the surface and an antimicrobial effect due to liberating the antimicrobial metal ion from an inside.

In this embodiment, it is preferred that the above-mentioned antimicrobial metal layer in a metal state is an ion release-suppressing layer. When the antimicrobial solid material containing the antimicrobial metal ion is put into a liquid to be treated, the elution rate of the antimicrobial metal ion is too fast so that the antimicrobial metal ion is eluted out within a short period and exhausted in many cases. In the antimicrobial solid material of this type, the layer containing antimicrobial metal in a metal state supported onto the antimicrobial metal ion layer becomes a barrier material for elution of ions whereby the elution rate of the antimicrobial metal ion is lowered and an antimicrobial effect of said ion lasts long.

In this embodiment, it is further preferred that the above-mentioned ion release-suppressing layer further contains a photocatalyst. By utilizing a photoreductive catalytic action of the photocatalyst, an antimicrobial metal in a metal state can be effectively supported on the antimicrobial metal ion layer. Also, an antimicrobial action based on the photocatalytic action can be also expected.

In this embodiment, the above-mentioned ion release-suppressing layer may be made to have a function of automatically controlling an antimicrobial metal ion concentration in a liquid to be treated. Details of this function will be explained in Examples.

The antimicrobial solid material in other embodiments of the present invention is characterised in that the solid material has a substrate, a deep-layer antimicrobial metal ion layer supported to the substrate, an ion release-suppressing layer fixed on said antimicrobial metal ion layer and containing an antimicrobial metal in a metal state, and a surface-layer antimicrobial metal ion layer fixed on said ion release-suppressing layer.

In the antimicrobial solid material in this embodiment, a surface-layer antimicrobial metal ion layer is added. This layer shows, after throwing the antimicrobial solid material in a liquid to be treated, a potent antimicrobial effect by eluting out in the liquid to be treated rapidly. And, thereafter, the antimicrobial metal ion gradually liberating from the deep-layer antimicrobial metal ion layer through the ion release-suppressing layer.

The antimicrobial metal in the antimicrobial solid material of the present invention can be selected one kind or a plural kinds from silver, copper and zinc. These have an antimicrobial action and have admitted their safety to human body. Among these, copper has an excellent antifungal activity against fungi, while silver has an excellent antibacterial effect against bacteria. Accordingly, an antimicrobial solid material containing both of copper and silver is effective to almost all kinds of microorganisms.

A process for producing the antimicrobial solid material of the present invention comprises the steps of an ion applying step for applying an antimicrobial metal ion to the surface of a substrate, and a reducing step of reducing part of said antimicrobial metal ion to an antimicrobial metal in a metal state.

As a method of applying the antimicrobial metal ion, it is preferred to apply the antimicrobial metal ion by absorbing the antimicrobial metal ion to a porous substrate. In addition, various methods such as coating, spraying, adhering a film, and the like, can be employed.

In the above-mentioned reducing step, a reducing method by photoirradiation, sacrifice oxidant or heat treatment can be employed. Among these three methods, a method by photoirradiation is most preferred. Since three merits mentioned below are present when it is fixed by the photoreductive method.

First, only by changing the degree of photoreduction, both of an antimicrobial metal ion which is an antimicrobial component having a potent antimicrobial effect at an initial stage and an antimicrobial metal in a metal state which is an antimicrobial component having a bacteriostatic effect for a long term can be fixed with a predetermined ratio. This is because a reaction of reducing the antimicrobial metal ion by photoirradiation after coating a substance (salt, and the like) containing an antimicrobial metal ion on the photocatalyst proceeds gradually from an active point of the photocatalyst.

Second, by photoreduction, a fixed state with a suitable strength can be realized. Thus, when a sufficient antimicrobial effect and use for a long term are considered, the elution rate of the antimicrobial component can be maintained to a harmonious rate of both.

Third, fine particle antimicrobial metal with a size of 10 nm or so can be supported so that the antimicrobial metal is to be gradually released in a liquid with the state of such fine particles. Thus, when the liquid to be treated is circulating water or collected water, the gradually released antimicrobial metal is uniformly dispersed in the liquid so that it shows a sufficient bacteriostatic effect.

The process for producing the antimicrobial solid material as one embodiment of the present invention comprises the steps of a photocatalyst layer forming step which forms a porous photocatalyst layer on the surface of a porous substrate, soaking step of absorbing antimicrobial metal ions to the substrate to which said photocatalytic layer is formed, and an irradiation step of depositing antimicrobial metals in a metal state in the photocatalyst layer by irradiating light to the photocatalyst layer containing the antimicrobial metal ions.

According to this method, an antimicrobial solid material having an excellent antimicrobial activity can be produced relatively easily.

The antimicrobial treating method of a liquid which is one embodiment of the present invention is characterised in that placing an antimicrobial solid material having a substrate, an antimicrobial metal ion layer supported to the substrate, and an ion release-suppressing layer containing an antimicrobial metal in a metal state and fixed on said antimicrobial metal ion layer in a liquid to be treated, irradiating light having an ultraviolet ray to said antimicrobial solid material to control deposition of the antimicrobial metal in a metal state at the surface of the antimicrobial solid material whereby controlling a releasing amount of the antimicrobial metal ion into the liquid to be treated.

When irradiation of light is made strong, much amounts of the antimicrobial metal in a metal state are deposited to inhibit formation of the antimicrobial metal ion and passing thereof (from the antimicrobial metal ion layer to the liquid to be treated). When irradiation of light is made weak, reverse results are obtained. Thus, by changing the strength of irradiation of light, a releasing amount of the antimicrobial metal ion into the liquid to be treated can be controlled.

As the specific example of the above-mentioned treating method, there is a method that an antimicrobial solid material having a substrate, a silver ion and/or copper ion layer supported to the substrate, and an ion release-suppressing layer fixed on said ion layer is placed in a liquid to be treated so that said ion is gradually released into the liquid to be treated.

A water treating device of the present invention is characterised in that it has a packed layer with which various kinds of the antimicrobial solid materials of the present invention are filled.

In the packed layer, sterilization and killing microorganisms can be carried out stably for a long term.

A method for preventing dirt at a trap or a pop-up stopper of the present invention is characterised in that various kinds of the antimicrobial solid material of the present invention is provided to a drain trap or a pop-up stopper.

By sterilizing sewage contacting to the trap, and the like, or the surface of the trap, and the like, dirt of the trap, and the like, and occurrence of smell can be inhibited.

An antimicrobial solid material which is one of the other embodiments of the present intention is characterised in that it has an antimicrobial agent (initially effective antimicrobial agent) which releases potent antimicrobial component at an initial stage, and an antimicrobial agent (enduringly effective antimicrobial agent) which releases antimicrobial component having a bacteriostatic and fungistatic effects for a long term.

In the present invention, when an antimicrobial metal ion or a substance which releases an antimicrobial metal ion is used as the initially effective antimicrobial agent, antimicrobial metal ions having a sufficient antimicrobial effect spread to whole part of the liquid to be subjected so that it is preferred.

As the enduringly effective antimicrobial agent, an antimicrobial metal in a metal state or a substance containing an antimicrobial metal in a metal state is preferred by the reason as mentioned below.

The antimicrobial metal in the metal state released into a liquid is difficultly binded to cell membranes of microorganisms having a negative charge in the liquid and difficultly binded by DNA, and the like, in microorganisms as compared with the antimicrobial metal ion. Also, even when an anion (e.g., a halogen ion in the case where the antimicrobial metal is silver) which easily forms an insoluble salt with the antimicrobial metal ion exists in a liquid, the antimicrobial metal in a metal state difficultly reacts than the antimicrobial metal ion and difficultly forms a hardly soluble salt so that the antimicrobial activity thereof does not decline at all.

Further, even when a cation such as an alkali metal ion, an alkali earth metal ion, and the like, exists in a liquid, elution of the antimicrobial metal does not occur due to ion exchange with these ions so that the antimicrobial effect does not decline within a short period.

Accordingly, when the antimicrobial solid material is used in a circulating water or collected water, the antimicrobial metal in a metal state exists in a solution with a stabilized state so that the metal show an antimicrobial effect for a long term. In other word, the defect of the antimicrobial component such as the antimicrobial metal ion, and the like, that it is depended on surroundings while it has a strong sterilizing activity, is complemented by the antimicrobial metal in a metal state.

The antimicrobial metal in a metal state is preferably an average particle size of not more than 100 nm since it is easily dispersed in a liquid uniformly and easily dissolved as an ion.

In the antimicrobial solid material of the present invention, an initially effective antimicrobial agent and an enduringly effective antimicrobial agent are preferably fixed to the surface of a substrate. Such an antimicrobial solid material can endure a plural number of uses.

In the antimicrobial solid material of the present invention, it is preferably made that an initially effective antimicrobial agent and an enduringly effective antimicrobial agent are fixed on the surface of a substrate and the above-mentioned substrate is porous, and at least the above-mentioned initially effective antimicrobial agent is supported in the porous substrate.

After the initially effective antimicrobial agent fixed on the surface of the substrate was exhausted, the initially effective antimicrobial agent supported and fixed in the pores of the substrate is gradually released with delay through open pores existing in the enduringly effective antimicrobial agent so that it has an excellent antimicrobial activity for a long term. Accordingly, characteristics in a plural number of uses in collected water are also improved.

In the antimicrobial solid material of the present invention, it is more preferred that a layer comprising a substance having a photocatalytic function (a photocatalytic layer) is fixed on a surface of the substrate, and that the initially effective antimicrobial agent and the enduringly effective antimicrobial agent are fixed on said layer by the reasons as mentioned below.

Firstly, when a substance having a photocatalytic function is interposed, a photoreductive reaction is accelerated so that both of an antimicrobial metal ion and an antimicrobial metal in a metal state can be fixed to a substrate within a relatively short time.

Secondly, sterilization due to the photocatalytic function possessed by said substance itself is also expected.

BRIEF DESCRIPTION OF THE DRAWINGS

FIG. 5 is a schematic view showing another example of the present invention, and (a) is a whole view and (b) is an enlarged view.

FIG. 6 is a schematic view showing another example of the present invention, and (a) is a whole view and (b) is an enlarged view.

FIG. 7 is a schematic view showing another example of the present invention, and (a) is a whole view and (b) is an enlarged view.

FIG. 8 is a schematic view showing another example of the present invention, and (a) is a whole view and (b) is an enlarged view.

EXAMPLES

In the following, specific examples of the present invention will be explained based on the drawings.

Figure 1A:
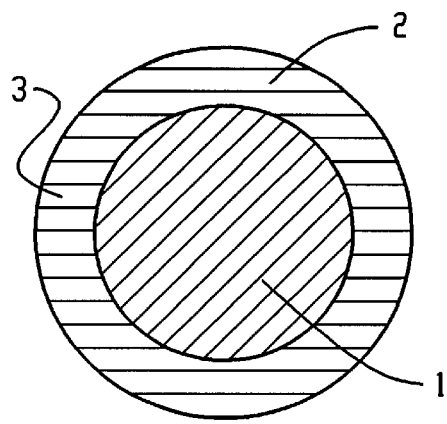
FIG. 1 is a schematic view showing an example of the present invention, and (a) is a whole view and (b) is an enlarged view.
Figure 1B:
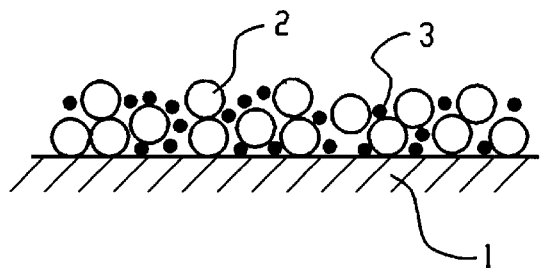

FIGS. 1(a) and (b) are schematic views showing one embodiment of the present invention. The antimicrobial solid material of this drawing comprises, on the surface of a substrate 1, a mixed layer of an initially effective antimicrobial agent (a component having strong bactericidal and fungicidal activity 3) and an enduringly effective antimicrobial agent (a bacteriostatic and fungistatic component 2) being formed.

Figure 2A:
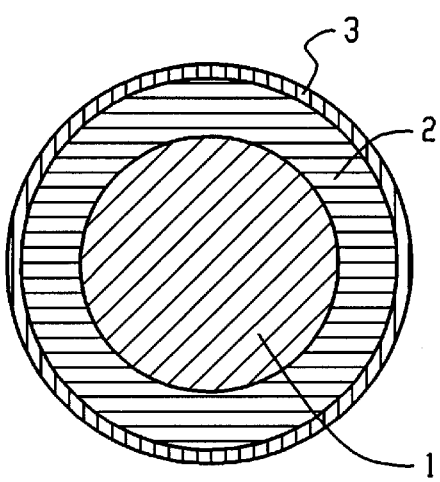
FIG. 2 is a schematic view showing another example of the present invention, and (a) is a whole view and (b) is an enlarged view.

FIGS. 2(a) and (b) are schematic views showing another embodiment of the present invention. The antimicrobial solid material of this drawing comprises, on the surface of a substrate 1, a layer comprising an enduringly effective antimicrobial agent 2 being formed, and further a layer comprising an initially effective antimicrobial agent 3 being formed thereon.

Figure 3A:
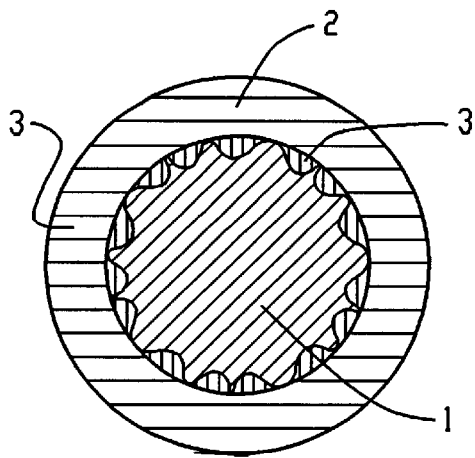
FIG. 3 is a schematic view showing another example of the present invention, and (a) is a whole view and (b) is an enlarged view.
Figure 3B:
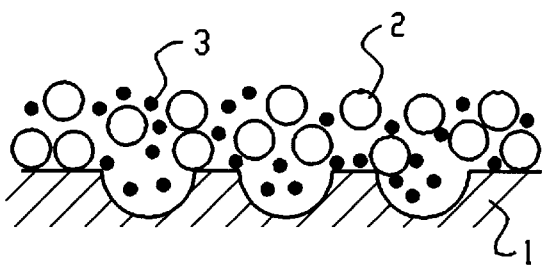

FIGS. 3(a) and (b) are schematic views showing another embodiment of the present invention. The antimicrobial solid material of this drawing comprises, an initially effective antimicrobial agent 3 being absorbed to a porous substrate 1, and further a mixed layer of an initially effective antimicrobial agent 3 and an enduringly effective antimicrobial agent 2 being formed on the surface of the substrate 1.

Figure 4A:
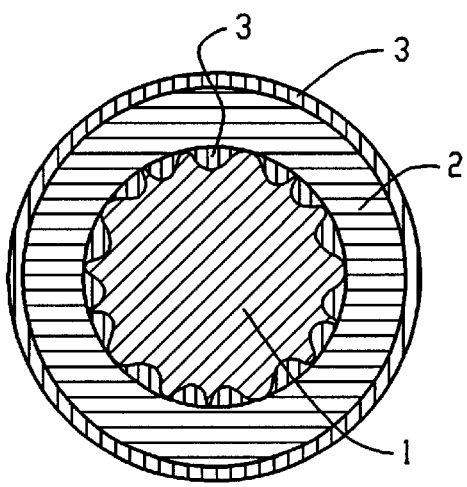
FIG. 4 is a schematic view showing another example of the present invention, and (a) is a whole view and (b) is an enlarged view.
Figure 4B:
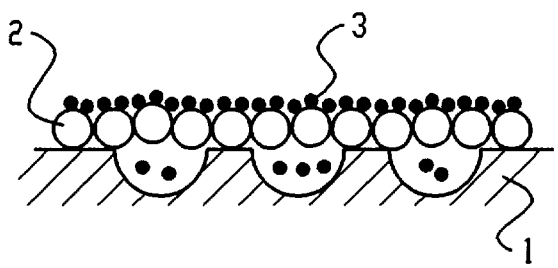

FIGS. 4(a) and (b) are schematic views showing another embodiment of the present invention. The antimicrobial solid material of this drawing comprises, an initially effective antimicrobial agent 3 being absorbed to a porous substrate 1, a layer comprising an enduringly effective antimicrobial agent 2 being formed, and further a layer comprising an initially effective antimicrobial agent 3 being formed thereon.

FIGS. 5(a) and (b) are schematic views showing another embodiment of the present invention. The antimicrobial solid material of this drawing comprises, on the surface of a substrate 1, a layer 4 comprising a substance having a photocatalytic function being formed, and further a mixed layer of an initially effective antimicrobial agent 3 and an enduringly effective antimicrobial agent 2 being formed thereon.

FIGS. 6(a) and (b) are schematic views showing another embodiment of the present invention. The antimicrobial solid material of this drawing comprises, on the surface of a substrate 1, a layer 4 comprising a substance having a photocatalytic function being formed, a layer comprising an enduringly effective antimicrobial agent 2 being formed, and further a layer comprising an initially effective antimicrobial agent 3 being formed thereon.

FIGS. 7(a) and (b) are schematic views showing another embodiment of the present invention. The antimicrobial solid material of this drawing comprises, an initially effective antimicrobial agent 3 being absorbed to a porous substrate 1, a layer 4 comprising a substance having a photocatalytic function being formed thereon, and further a mixed layer of an initially effective antimicrobial agent 3 and an enduringly effective antimicrobial agent 2 being formed thereon.

FIGS. 8(a) and (b) are schematic views showing another embodiment of the present invention. The antimicrobial solid material of this drawing comprises, an initially effective antimicrobial agent 3 being absorbed to a porous substrate 1, a layer 4 comprising a substance having a photocatalytic function being formed thereon, a layer comprising an enduringly effective antimicrobial agent 2 being formed thereon, and further a layer comprising an initially effective antimicrobial agent 3 being formed thereon.

Here, the initially effective antimicrobial agent means an antimicrobial agent containing an antimicrobial component having a potent killing microorganisms immediately after released into a liquid to be treated. The term initial herein mentioned means a relatively short term after the antimicrobial component is gradually released into a liquid. As an example of the antimicrobial component having such a characteristic, there may be mentioned an antimicrobial metal ion such as a silver ion, a copper ion, a zinc ion, and the like, hypochlorous acid, ozone, ozone-containing water, acidic water, and the like. Each of which shows a potent antimicrobial activity within a relatively short term after the antimicrobial component was gradually released into a liquid. However, particularly in a collected liquid, the antimicrobial agent containing these antimicrobial components has a characteristic of lowering the antimicrobial activity with a lapse of time. The cause can be considered due to, in the case of an antimicrobial metal ion, as in a halogen ion, and the like, in the case of a silver ion, the reaction with insoluble salt or a complex salt having a little bactericidal effect, or with a substance existing in a solution capable of easily forming a complex ion, or binding to bacteria having a negative charge to a cell membrane, and the like. Also, in hypochlorous acid, ozone, and the like, it can be considered that they are easily combined or reacted with an organic component in a solution. Further, it can be considered that the antimicrobial component is easily released out from the antimicrobial materials.

In the present invention, in order to complement the matter, an antimicrobial agent (an enduringly effective antimicrobial agent) which releases an antimicrobial component having bacteriostatic and fungistatic effects for a long term is mixed in an antimicrobial solid material. Here, the long term means that the term in which an antimicrobial component can maintain bacteriostatic and fungistatic effects stably after release into a liquid to be treated is long. The bacteriostatic and fungistatic effect means an antimicrobial effect of such a degree that bacteria and fungi are not increased. In an antimicrobial component having such a characteristic, there may be mentioned an antimicrobial metal such as a metal state silver, copper, zinc, and the like, a hardly soluble metal compound having an antimicrobial effect such as cuprous oxide, and the like. The antimicrobial component herein mentioned is inferior in bactericidal and fungicidal effect as compared with the antimicrobial component which shows potent bactericidal and fungicidal effect at an initial stage as mentioned above, but has characteristics of low reactivity with microorganisms, fungi, organic components, ions, and the like, and chemically stable in a treating liquid. Accordingly, by copresenting such antimicrobial components, even when an antimicrobial effect cannot be maintained for a long term by an action of only an initially effective antimicrobial agent, an antimicrobial effect can be maintained for a long term.

As the antimicrobial component in the initially effective antimicrobial agent, antimicrobial metal ions are particularly preferred. This is because the antimicrobial metal ion can be easily supported and fixed in the solid material as compared with hypochlorous acid, ozone, and the like. Also, the antimicrobial metal ion can be taken out only a necessary amount from the solid material in which said ion is supported and fixed by controlling an ion release rate so that it can easily endure for a long term use. In the antimicrobial metal ion, there are a silver ion, a copper ion, a zinc ion, and the like. Among them, the silver ion is strong in effects against bacteria as compared to the others, and the copper ion is strong in effects against fungi as compared to the others, so that it is desired that both ions are suitably selected or both are copresent to use.

As an antimicrobial agent releasing the antimicrobial metal ion, a substance which contains the antimicrobial metal ion can be used. As the substance containing the antimicrobial metal ion, there may be specifically mentioned compounds containing a soluble antimicrobial metal element such as silver lactate, silver nitrate, silver acetate, silver sulfate, cuprous acetate, cupric acetate, copper nitrate, cuprous sulfate, cupric sulfate, zinc acetate, zinc nitrate, zinc chloride, zinc sulfate, and the like, or apatite, calcium phosphate, zirconium phosphate, aluminum phosphate, titania, layered silicate, layered aluminosilicate, zeolite on which the antimicrobial metal ion is supported, and the like.

Material of the substrate may be basically any material such as ceramic, a pottery material, metal, glass, plastic or a composite material thereof, and the like. However, when the above-mentioned two kinds of antimicrobial agents are fixed through particles comprising a substance having a photocatalytic function, it is necessary to carry out heat treatment at a high temperature of 300° C. or higher so that ceramic or a pottery material which are excellent in thermal stability are preferred. Also, particularly in the case of ceramic, a pottery material and metal, it is preferably porous in the viewpoint of light-weight.

Specific examples of a step for preparing a porous substrate are as follows when the substrate is a pottery material or ceramic.

① A component (for example, an organic binder) having a predetermined particle size and decomposed by baking is added to a green powder comprising components constituting a substrate with a predetermined amount and the mixture is sintered wherein a pore size and porosity of the substrate is controlled by the particle size and the amount of the added decomposing component.

② A starting material which is hardly densed is used as a starting material of components constituting a substrate to increase the porosity and the pore size is controlled by using fine particles (for example, fine particle active alumina ($\gamma$-$Al_2O_3$, bemite, and the like) is used).

③ Among the component constituting the substrate, an amount of a component forming a liquid phase (silica, alkaline earth metal component, and the like) is regulated to control a porosity. In this method, a pore size is controlled by the manner of filling a molded material.

The shape of the substrate may be any of sphere, columnar, cylindrical, prism, hollow prism, rod, plate, powder, bulk, and the like. In a dimensional view, in the point of easy handling, it preferably has a size each of which can grasp with fingers. Also, the corner and edge portions are preferably not sharpened. The reason is mentioned that, when the corner and edge portions are present, attached conditions of the above-mentioned two kinds of antimicrobial agents to these portions are easily changed, and these portions are mechanically weak whereby peeling off or elution is predominantly caused so that ununiform elution occurs. Also, the symmetrical solid shapes such as sphere, columnar, cylindrical, prism, rod, plate, and the like, are excellent in the point that the above-mentioned two kinds of antimicrobial agents are easily and uniformly attached, while in cylindrical, hollow prism shape, there is a merit of lightening the parts.

Carrying the antimicrobial agent or the substance having a photocatalytic function on the substrate may be direct carrying or indirect carrying through an adhesion layer. Here, a material of the adhesion layer may be any of inorganic thermoplastic materials such as glaze, and the like, inorganic thermosetting materials such as a silicone resin, and the like, organic thermoplastic materials such as an acrylic resin, and the like, and organic thermosetting materials such as an epoxy resin, and the like.

The layer comprising a substance having a photocatalytic function means a layer mainly comprising particles having a photocatalytic function. This layer may contain a small amount of particles having no photocatalytic function. As such particles, there may be mentioned a baking aid to be added for improving the strength of said layer, and the like.

The layer comprising a substance having a photocatalytic function may be formed on the whole surface of the substrate or may be formed on part thereof. However, when it is formed on the whole surface, an amount of the antimicrobial agent supported on the substrate can be increased and no terminal end exists so that peeing off or elution do not occur predominantly from the portion whereby it is preferred.

The substance (particles) having a photocatalytic function is sufficient when it has a band gap with a degree that an antimicrobial metal can be reduced and deposited from a solution of a salt containing an antimicrobial metal element at photoirradiation. As such a material, there may be mentioned titanium oxide, zinc oxide, tungsten trioxide, ferric oxide, strontium titanate, dibismuth trioxide, tin oxide, silicon carbide, gallium phosphide, cadmium sulfide, cadmium selenide, silicon, gallium arsenide, indium phosphide, cadmium telluride, molybdenum trisulfide, and the like.

Also, the substance having a photocatalytic function itself may have an antimicrobial activity. In the reason why a semiconductor having a photocatalytic function has an antibacterial activity, there is an opinion that not less than a predetermined voltage is applied to cause death by an electric shock (Japanese Patent Publication No. 29393/1992), but it is generally considered that an active oxygen caused at photoirradiation generates an antimicrobial action. According to this opinion, to have an antimicrobial activity, i.e., to form an active oxygen, it is necessary that the position of a conductive band of a semiconductor, which is denoted by a band model, locates upper than a hydrogen generating potential and the upper end of a valence electron band is below than an oxygen generating potential. As a semiconductor which satisfies the conditions, there are titanium oxide, zinc oxide, strontium titanate, silicon carbide, gallium phosphide, cadmium sulfide, cadmium selenide, and the like. Also, when the particle is made fine, the position of a conductive band transfers to upper portion. Thus, if the layer can be constituted by fine particles with 1 to 10 nm or so, there is a possibility that tungsten trioxide, ferric oxide, dibismuth trioxide, tin oxide, and the like, have an antimicrobial activity. Incidentally, particles comprising a substance having a photocatalytic function may be constituted by one kind of a substance, or may be constituted by two or more kinds of substance.

Next, processes for producing an antimicrobial solid material shown in FIGS. 1 to 8 are explained.

First, as for the process for producing an antimicrobial solid material which comprises forming a mixed layer of an initially effective antimicrobial agent and an enduringly effective antimicrobial agent on the surface of a substrate shown in FIGS. 1(a) and (b), explanation is carried out by taking, as an example, the case where the substrate is alumina, the initially effective antimicrobial agent is silver nitrate, and the enduringly effective antimicrobial agent is silver in a metal state.

One method is a method in which a silver nitrate solution is coated on an alumina substrate, and light is irradiated for a predetermined time. According to this method, by photoirradiation, silver ions in silver nitrate are gradually reduced. Accordingly, if a photoirradiation time is suitably selected, silver nitrate releasing silver ions which are antimicrobial components initially potent in bactericidal activity, and silver in a metal state which is an enduringly effective antimicrobial agent are copresent on the surface of the alumina substrate whereby the solid material shown in FIG. 1 can be obtained.

As the other method, there is a method in which a silver nitrate solution is coated on the alumina substrate, and then a suitable amount of a sacrifice oxidant such as an alcohol, aldehyde, reduced sugar, and the like, is added thereto. According to this method, an oxidized amount of the above-mentioned sacrifice oxidant is the same as a reduced amount of silver ions in silver nitrate. Accordingly, by controlling the amount of the sacrifice oxidant to be added, silver nitrate releasing silver ions which are antimicrobial components initially potent in bactericidal activity, and silver in a metal state which is an enduringly effective antimicrobial agent are copresent on the surface of the alumina substrate whereby the solid material shown in FIG. 1 can be obtained.

As the other method, there is a method in which a silver nitrate solution is coated on the alumina substrate, and then they are reduced by subjecting to heat treatment. According to this method, silver ions in silver nitrate are reduced by the heat treatment. Accordingly, by suitably selecting a heat treatment time, silver nitrate releasing silver ions which are antimicrobial components initially potent in bactericidal activity, and silver in a metal state which is an enduringly effective antimicrobial agent are copresent on the surface of the alumina substrate whereby the solid material shown in FIG. 1 can be obtained. As the further method, reduction by electroplating can be considered.

Next, as for the process for producing an antimicrobial solid material which comprises forming a layer comprising an enduringly effective antimicrobial agent on the surface of a substrate, and further forming a layer comprising an initially effective antimicrobial agent thereon as shown in FIG. 2(a) and (b), explanation is carried out by taking, as an example, the case where the substrate is alumina, the initially effective antimicrobial agent is silver nitrate, and the enduringly effective antimicrobial agent is silver in a metal state.

Figure 2B:
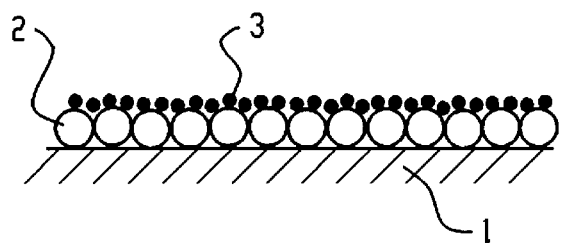

The preparation method of this case is carried out by, for example, coating a silver nitrate solution on an alumina substrate, and after reducing silver ions by the above-mentioned three methods (reduction by photoirradiation, reduction using a sacrifice oxidant, reduction by heat treatment), and the like, and a silver nitrate solution is further coated and dried to form an unreduced silver nitrate layer thereon, whereby the solid material shown in FIG. 2 can be obtained.

Next, as for the process for producing an antimicrobial solid material which comprises impregnating an initially effective antimicrobial agent to a porous substrate, and further forming a mixed layer of an initially effective antimicrobial agent and an enduringly effective antimicrobial agent on the surface of a substrate as shown in FIG. 3(a) and (b), explanation is carried out by taking, as an example, the case where the substrate is alumina, the initially effective antimicrobial agent is silver nitrate, and the enduringly effective antimicrobial agent is silver in a metal state.

The preparation method of this case is as follows. For example, a porous alumina substrate is dipped in a silver nitrate solution, and, if necessary, while carrying out vacuum deaeration treatment, silver nitrate is absorbed into the substrate. At this time, silver nitrate is also attached to the substrate. Further, the sample is pulled up, and dried, then light is irradiated to silver nitrate attached which is exposed on the surface of the substrate for a predetermined time, part of silver ions in silver nitrate at the portion is reduced whereby the solid material shown in FIG. 3 can be obtained.

As for the process for producing an antimicrobial solid material which comprises absorbing an initially effective antimicrobial agent to a porous substrate, forming a layer comprising an enduringly effective antimicrobial agent on the surface of the substrate, and further forming a layer comprising an initially effective antimicrobial agent thereon as shown in FIGS. 4(a) and (b), explanation is carried out by taking, as an example, the case where the substrate is alumina, the initially effective antimicrobial agent is silver nitrate, and the enduringly effective antimicrobial agent is silver in a metal state.

The preparation method of this case is carried out by, for example, dipping a porous alumina substrate in a silver nitrate solution to absorb silver nitrate into the substrate, by subjecting to vacuum deaeration treatment, if necessary. At this time, silver nitrate is also attached to the substrate. Further, the sample is pulled up, and dried, then light is irradiated to silver nitrate attached which is exposed on the surface of the substrate for a predetermined time, part of silver ions in silver nitrate at the portion is reduced. Thereafter, a silver nitrate solution is further coated and dried to form an unreduced silver nitrate layer is formed thereon whereby the solid material shown in FIG. 4 can be obtained.

As for the process for producing an antimicrobial solid material which comprises forming a layer comprising a substance having a photocatalytic function on the surface of a substrate, and further forming a mixed layer of an initially effective antimicrobial agent and an enduringly effective antimicrobial agent thereon as shown in FIGS. 5(a) and (b), explanation is carried out by taking, as an example, the case where the substrate is alumina, the substance having a photocatalytic function is an anatase type titanium oxide, the initially effective antimicrobial agent is silver nitrate, and the enduringly effective antimicrobial agent is silver in a metal state.

The preparation method of this case is as follows. First, on the surface of a substrate, a substance having a photocatalytic function or a precursor thereof is coated. Here, the precursor means a sol of the substance having a photocatalytic function, or a substance which changes to the substance having a photocatalytic function such as an alkoxide, an organic acid salt, an inorganic acid salt, and the like containing a metal element in the substance having a photocatalytic function. For example, a sol suspension of titanium oxide is coated. Thereafter, the material is baked at 300 to 900° C. to form a titanium oxide layer, a silver nitrate solution is coated onto the titanium oxide layer and light is irradiated for a predetermined time. According to this method, by photoirradiation, silver ions in silver nitrate are reduced within a short time as compared with the case where no titanium oxide layer is present whereby the solid material shown in FIG. 5 can be obtained.

As for the process for producing an antimicrobial solid material which comprises forming a bottom layer comprising a substance having a photocatalytic function on the surface of a substrate, forming a middle layer comprising an enduringly effective antimicrobial agent thereon, and further forming an upper layer comprising an initially effective antimicrobial agent thereon as shown in FIGS. 6(a) and (b), explanation is carried out by taking, as an example, the case where the substrate is alumina, the substance having a photocatalytic function is an anatase type titanium oxide, the initially effective antimicrobial agent is silver nitrate, and the enduringly effective antimicrobial agent is silver in a metal state.

The preparation method of this case is as follows. For example, on the surface of a substrate, a sol suspension of titanium oxide is coated, and then, the material is baked at 300 to 900° C. to form a titanium oxide layer. Then, a silver nitrate solution is coated onto the titanium oxide layer and light is sufficiently irradiated to reduce silver ions in silver nitrate. Thereafter, a silver nitrate solution is further coated onto the reduced silver layer and dried so that an unreduced silver nitrate layer is formed on the reduced silver layer whereby the solid material shown in FIG. 6 can be obtained.

As for the process for producing an antimicrobial solid material which comprises absorbing an initially effective antimicrobial agent to a porous substrate, forming a layer comprising a substance having a photocatalytic function on the surface of a substrate, and further forming a mixed layer of an initially effective antimicrobial agent and an enduringly effective antimicrobial agent thereon as shown in FIGS. 7(a) and (b), explanation is carried out by taking, as an example, the case where the substrate is alumina, the substance having a photocatalytic function is an anatase type titanium oxide, the initially effective antimicrobial agent is silver nitrate, and the enduringly effective antimicrobial agent is silver in a metal state.

The preparation method of this case is as follows. For example, on the surface of a porous alumina substrate, a sol suspension of titanium oxide is coated, and then, the material is baked and fixed at 300 to 900° C. Thereafter, the sample is dipped in a silver nitrate solution, and, if necessary, while carrying out vacuum deaeration treatment, silver nitrate is absorbed into the substrate. At this time, silver nitrate is also attached to the substrate. At this time, simultaneously, light is sufficiently irradiated to the attached silver nitrate exposed to the surface of the substrate to reduce part of silver ions in a silver nitrate, or thereafter, pulling up the sample, light is sufficiently irradiated to the sample surface to reduce part of silver ions in silver nitrate whereby the solid material shown in FIG. 7 can be obtained. Here, before coating the titanium oxide sol, silver ions may be absorbed into the substrate. The specific method is to absorb silver nitrate into the substrate.

As for the process for producing an antimicrobial solid material which comprises absorbing an initially effective antimicrobial agent to a porous substrate, forming a layer comprising a substance having a photocatalytic function thereon, forming a layer comprising an enduringly effective antimicrobial agent thereon, and further forming a layer comprising an initially effective antimicrobial agent thereon as shown in FIGS. 8(a) and (b), explanation is carried out by taking, as an example, the case where the substrate is alumina, the substance having a photocatalytic function is an anatase type titanium oxide, the initially effective antimicrobial agent is silver nitrate, and the enduringly effective antimicrobial agent is silver in a metal state.

The preparation method of this case is as follows. For example, on the surface of a porous alumina substrate, after a sol suspension of titanium oxide is coated, the material is baked and fixed at 300 to 900° C. Thereafter, the porous alumina substrate is dipped in a silver nitrate solution, and, if necessary, while carrying out vacuum deaeration treatment, silver nitrate is absorbed into the substrate. At this time, silver nitrate is also attached to the substrate. At this state, when light is irradiated from the upper surface of an apparatus for a predetermined time, part of silver nitrate attached to the substrate is reduced. Thereafter, without irradiating light, or changing light to weak intensity of illumination at an ultraviolet region, the material is further dipped in a silver nitrate solution, an unreduced silver nitrate is attached whereby the solid material shown in FIG. 8 can be obtained.

In the following, an antimicrobial solid material which is another embodiment of the present invention is explained.

As conventionally known, when silver powder in a metal state was used, the antimicrobial effect was not sufficient at the contacting portion of an instrument when the subject is a flowing water circumstance, or in the case of a circulating water or collected water existing a plenty amount of nutrient source such as bouillon, and the like.

Here, the reason why the antimicrobial effect at the contacting portion of an instrument when the subject is a flowing water circumstance is not sufficient can be considered that since the absolute antimicrobial activity of silver powder in the metal state is weaker than that of silver ions, the silver powder does not stay at one part of the contacting portions of the instrument for such a long time that will be required to conduct a sufficient antimicrobial action.

Also, the reason why the antimicrobial effect is not sufficient when the subject is a circulating water or collected water in which a plenty amount of nutrient source is existed such as bouillon, and the like, can be considered that, particularly when an initial number of microorganisms is relatively large, an antimicrobial activity of silver powder is not so potent as to sufficiently inhibit growth of microorganisms.

An object of the present invention is, in view of the above circumstance, to provide a solid material having a sufficient antimicrobial activity for a long term against various forms of sewage in circulating water, collected water and flowing water, and at the contacting portion.

The antimicrobial solid material which is one embodiment of the present invention is characterised in that a storage portion of an antimicrobial component, and an suppressing layer which inhibits release of the antimicrobial component from said storage portion are provided. This antimicrobial solid material may further have a surface layer which releases the antimicrobial component.

In the present invention, the solid material has a storage portion of an antimicrobial component having a potent antimicrobial activity and a layer which inhibits release of the antimicrobial component having a potent bactericidal activity from said storage portion. Accordingly, at the storage portion of an antimicrobial component having a potent antimicrobial activity, a large amount of the antimicrobial component having a potent antimicrobial activity can be stored, and also, diffusion of the antimicrobial component having a potent antimicrobial activity outward can be inhibited by the layer inhibiting release of the antimicrobial component so that it has an antimicrobial activity to each of flowing water, collected water and circulating water sufficiently for a long term.

Further, in addition to the storage portion of an antimicrobial component having a potent antimicrobial activity and a layer which inhibits release of the antimicrobial component having a potent antimicrobial activity from said storage portion, a surface layer which releases an antimicrobial component having a potent antimicrobial activity is provided, an antimicrobial activity at an initial stage can be strengthened, and it can cope with antimicrobial treatment at the portion in which growth of bacteria at an initial stage is particularly remarkable so that it is preferred.

In the following, explanation is carried out based on the drawings.

Figure 17A:
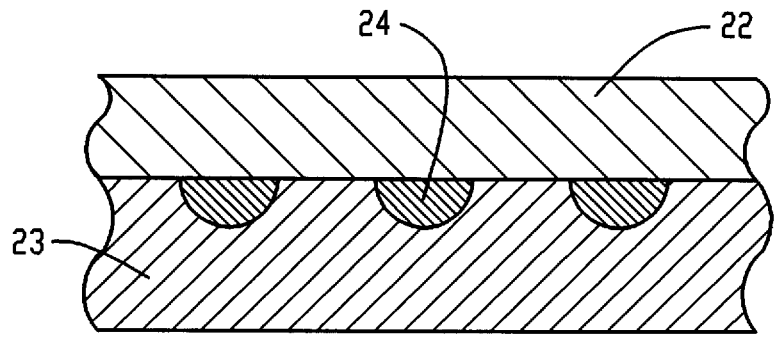
FIG. 17 is a schematic drawing showing a surface structure of an antimicrobial solid material according to an example of the present invention.
Figure 17B:
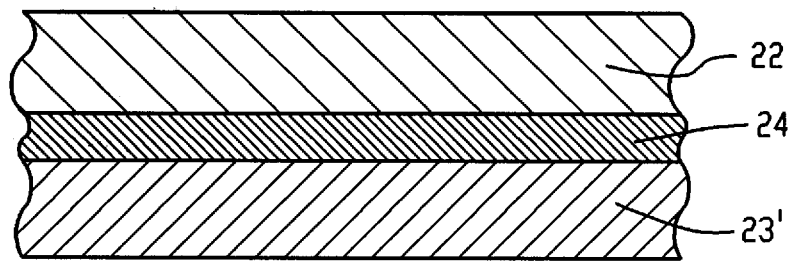

FIG. 17 is a drawing showing one embodiment of the present invention. In the antimicrobial solid material of FIG. 17(*a*), an antimicrobial component 24 having a potent antimicrobial activity is stored at a porous substrate 23, and a layer 22 which inhibits release of the antimicrobial component having a potent bactericidal activity is formed on the surface thereof. In the antimicrobial solid material of FIG. 17(*b*), a layer of an antimicrobial component 24 having a potent antimicrobial activity is formed on a dense substrate 23', and further a layer 22 which inhibits release of the antimicrobial component having a potent antimicrobial activity is formed on the surface thereof.

Figure 18:
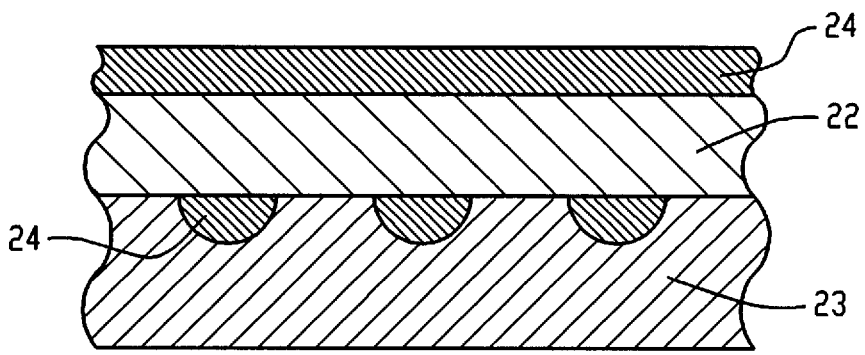
FIG. 18 is a schematic drawing showing a surface structure of an antimicrobial solid material according to an example of the present invention.

FIG. 18 is a drawing showing another embodiment of the present invention. In the antimicrobial solid material of this drawing, an antimicrobial component 24 having a potent antimicrobial activity is stored at a porous substrate 26, a layer 22 which inhibits release of the antimicrobial component having a potent antimicrobial activity is formed on the surface thereof, and further a surface layer 24 which releases an antimicrobial component having a potent antimicrobial activity is provided on the surface thereof.

Here, the antimicrobial component having a potent antimicrobial activity means, when it is gradually released into a liquid to be treated, an antimicrobial component having a remarkable antimicrobial effect at least immediately after gradual release. Such an antimicrobial component includes an antimicrobial metal ion such as a silver ion, a copper ion, a zinc ion, and the like, and a hypochlorous acid, ozone, ozone-containing water, acidic water, and the like. The antimicrobial metal ion may be stored as an antimicrobial metal ion, or may be stored as a substance containing an antimicrobial metal ion.

The layer which inhibits release of the antimicrobial component having a potent antimicrobial activity may be basically any structure so long as it has a structure of delaying a diffusion rate outward of the antimicrobial component having a potent antimicrobial activity supported to an open pore of the porous substrate. For example, there may be mentioned a layer existing fine pores, a layer easily absorbing the antimicrobial component having a potent antimicrobial activity, and the like.

The material of the layer which inhibits release of the antimicrobial component having a potent antimicrobial activity may be also basically any material, and, for example, there may be mentioned a substance having a photocatalytic function, an antimicrobial metal in a metal state, a composite layer thereof, and the like.

Here, the substance having a photocatalytic function means a substance which forms an electron and a hole by irradiation of light with a certain wavelength or less and as the results, proceeds formation of active oxygen, reduction of a metal, decomposition of a halide, and the like. As such a material, there may be mentioned titanium oxide, zinc oxide, strontium titanate, tungsten trioxide, ferric oxide, dibismuth trioxide, tin oxide, and the like.

To the substance having a photocatalytic function may be added a metal having an electron trapping effect in order to increase its activity. Here, the metal having an electron capturing effect means a metal having an energy level of a conductive band bottom end to a positive side than an energy level of a conductive band bottom end possessed by a photocatalytic substance such as platinum, copper, silver, palladium, gold, iron, nickel, cobalt, zinc, and the like.

In the following, specific evaluation experiments are explained.

Evaluation Experiment 1

As a substrate of a sample, a porous alumina substrate with a ball state having a diameter of 5 mm and an open pore rate of 62 volume % was prepared. To the substrate was coated whole surface an ammonia peptization type titanium oxide sol having an average particle size of 0.01 μm by a spray coating method. As to the substrate to which this titanium sol had been coated, the step of baking at 700 kC for one hour was repeated twice. Thereafter, the baked sample was dipped in a 1% by weight aqueous silver nitrate solution to absorb silver ions into the sample. Then, at the state of dipping the sample, a black blue (BLB) lamp was irradiated to the sample for 2 hours while rolling the sample by the shaking method whereby the silver ions were reduced and silver in a metal state was fixed to the surface of the substrate. After fixing the silver, excess silver was removed by ultrasonic washing, and then, the sample was well washed with water and dried to give a solid material Sample A.

The crystal type of the titanium oxide fixed on the obtained solid material was an anatase. The size of the silver particles was several nm to 10 nm. In the solid material, fine pores having an average of 10 nm or so were observed by a porosimeter with a large number. It was confirmed that in the fixed silvers, both of 0 valence and monovalence existed.

Also, for comparison, four samples shown below were prepared. One is a ball state silver granular Sample B having a diameter of 5 mm, one is Sample C in which metal silver is supported to apatite, one is Sample D in which silver ions are supported to zeolite by an ion exchange method, and the remaining one is Sample E in which silver complex ions are supported to silica gel.

With regard to these samples, initial antibacterial activities, and antibacterial activities after using for a long term were evaluated.

The initial antibacterial activity was evaluated as mentioned below. First, a solid material sample was dipped in a 80% by volume ethanol for 2 hours, then dried it at 50° C. and the surface was washed. Simultaneously, a bacterial suspension of Escherichia coli (E. coli) was prepared in an amount of $10^5$ CFU and added to an artificial urine (its composition is shown in Table 1) to prepare a test liquid. To the test liquid were placed each 10 respective solid material samples, and after allowing the test liquid to stand in an incubator at 30° C. for 24 hours, the number of bacteria in the test liquid was measured.

TABLE 1

Composition of artificial urine

| Composition | Weight (g) |
| --- | --- |
| $CaCl_2 \cdot 2H_2O$ | 0.65 |
| $MgCl_2 \cdot 6H_2O$ | 0.65 |
| $NaCl_2$ | 4.6 |
| $Na_2SO_4$ | 2.3 |
| Sodium citrate | 0.65 |
| Sodium oxalate | 0.02 |
| $KH_2PO_4$ | 2.8 |
| KCl | 1.6 |
| $NH_4Cl$ | 2.0 |
| Urea | 12.0 |
| Creatinine | 1.1/1 |
| Bouillon | 40 ml |
| pH 5.7–5.8 | |

Antibacterial activity after using for a long term was evaluated as mentioned below. First, a solid material sample was dipped in a 80% by volume ethanol for 2 hours, then dried it at 50° C. and the surface was washed. Next, in a sterilized beaker were placed 2 liters of the artificial urine and each 10 various solid material samples, and it was allowed to stand for one month whereby a long term used state was tentatively realized. Thereafter, the solid material sample was taken out and sterilized in an autoclave at 121° C. for 20 minutes. Then, it was dipped in a 80% by volume ethanol for 2 hours, then dried it at 50° C. and the surface was washed. Then, to the above test liquid were placed each 10 respective solid material samples, and after allowing the test liquid to stand in an incubator at 30° C. for 24 hours, the number of bacteria in the test liquid was measured.

The evaluation results of the antibacterial activity are shown in Table 2.

TABLE 2

Results of antibacterial activity evaluation experiment 1

| Sample | Initial antibacterial activity | Antibacterial activity after long term use |
| --- | --- | --- |
| A (Example of this invention) | <10 CFU | $10^2 \sim 10^3$ CFU |
| B (Metal silver granule) | $10^3 \sim 10^4$ CFU | $10^8 \sim 10^8$ CFU |
| C (Apatite metal silver fixed) | $10^2 \sim 10^3$ CFU | $10^7 \sim 10^8$ CFU |
| D (Zeolite silver ion fixed) | <10 CFU | $10^8 \sim 10^9$ CFU |
| E (Silica gel silver ion fixed) | <10 CFU | $10^8 \sim 10^9$ CFU |

In Samples A, D and E containing silver ions, the initial antibacterial activities were decreased to not more than 10 CFU and showed excellent bactericidal activities. To the contrary, in Samples B and C comprising metal silver particles, it was decreased only by $10^2$ to $10^4$ CFU or so whereby it could be found that these samples showed a certain degree of antibacterial activities but did not have sufficient bactericidal activities.

As for the antibacterial activities after a long term use, Samples D and E which do not contain any antibacterial component having an enduring bacteriostatic effect such as metal silver, and the like, did not show antibacterial activity and the number of bacteria rather increased 1,000 to 10,000 times of the initial bacteria number. Also, in Samples B and C comprising metal silver particles, the number of bacteria is less than those of Samples D and E and a slight enduring bacteriostatic effect was observed, but the number of bacteria increased 100 to 1,000 times of the initial bacteria number. To the contrary, in the solid material Sample A, the number of survival bacteria decreased until 1/100 to 1/1,000 or so based on the initial bacteria number and an excellent antibacterial activity was maintained for a long term. From the results of comparison with Samples B to E, it was found that Sample A had excellent antibacterial activities at initial and after long term use. The reason is considered that the solid material Sample A contains both of silver ions having a potent bactericidal activity at an initial stage and metal silver having a enduring bacteriostatic effect. Also, it can be considered that the layer of metal silver fixed by photoirradiation becomes a release-suppressing layer of silver ions absorbed into the substrate and is useful for gradually releasing the silver ions with a suitable rate.

Evaluation Experiment 2

Two forms of porous alumina substrates as mentioned below were prepared.

Rod: 10 mm in diameter×74 mm in length, open porosity 55% by volume,

Ball: 5 mm in diameter, open porosity 62% volume %,

The rod was obtained by adding baking aids such as clay, calcium carbonate, and the like, to α-$Al_2O_3$ powder and baking the mixture. The open porosity was controlled by changing an amount of the baking aids. The ball was prepared by using active alumina ($\gamma$-$Al_2O_3$) as a main component of the starting material to obtain a porous substrate.

The resulting baked bodies were analyzed by powder X-ray diffraction, and in the rod, almost all the part was corundum ($\alpha$-$Al_2O_3$) and minute amounts of mullite and anorthite were formed. In the ball, it was constituted by poor crystallizability $\gamma$-$Al_2O_3$ and quartz.

Respective substrates were dipped in an aqueous silver nitrate solution for 2 hours, and then pulled up and dried by irradiating light. By the step, Samples F (rod) and G (ball) containing silver ions as well as having metal silver (reduced) were prepared.

Further, to each of the other rod state substrate and ball state substrate was coated an ammonia peptization type titanium oxide sol having an average particle size of 0.01 $\mu$m by the spray coating method, and the samples were each baked at 750° C. for 2 hours to fix an anatase type titanium oxide on the substrate. Thereafter, these substrates were dipped in an aqueous silver nitrate solution for 2 hours while irradiating a BLB lamp from an upper direction of the aqueous solution apparatus to fix reduced silver and silver ions, and dried to prepare Samples H (rod) and I (ball).

As for the Samples F to I, open pore sizes and distribution thereof were measured by a porosimeter and the results are shown in Table 3. In F and H, an average open pore size is large while in G and I, an average size is small.

TABLE 3

Antibacterial activity evaluation experiment 2 Sample

| Sample | Shape | Average open pore size | Size distribution (nm) | Ratio less than 250 nm | Open porosity (volume %) |
|---|---|---|---|---|---|
| F | Rod | 1,330 nm | 40 ~ 1,750 | 20% | 55 |
| G | Ball | 19 nm | 8 ~ 1,370 | 70% | 62 |
| H | Rod | 1,020 nm | 20 ~ 2,900 | 28% | 55 |
| I | Ball | 10 nm | 3 ~ 320 | 88% | 62 |

By using these samples, antibacterial activity tests mentioned below were carried out and elution amounts of silver ions were also examined. The antibacterial activity test was carried out as mentioned below. First, into the artificial urine having the composition shown in Table 1, the above samples were added with two to F and H and ten to G and I, and further $10^4$ CFU/ml of *Escherichia coli* (*E. coli*) were inoculated. Dipping test for 24 hours was repeated 5 times. After dipping, as to the test liquids from which Samples F to I were removed, the numbers of survival bacteria and the silver ion concentrations were measured. The results concerning the number of survival bacteria are shown in Table 4 and the results concerning the silver ion concentration are shown in Table 5. Here, the silver ion concentration was measured by an atomic-absorption method.

TABLE 4

Evaluation experiment 2
Survival bacteria number

| Sample | First | Second | Third | Fourth | Fifth |
|---|---|---|---|---|---|
| F | $2 \times 10^4$ | $9 \times 10^4$ | $2 \times 10^4$ | $4 \times 10^4$ | $2 \times 10^3$ |
| G | $2 \times 10^4$ | $2 \times 10^4$ | $2 \times 10^4$ | $1 \times 10^4$ | $7 \times 10^3$ |

TABLE 4-continued

Evaluation experiment 2
Survival bacteria number

| Sample | First | Second | Third | Fourth | Fifth |
|---|---|---|---|---|---|
| H | $2 \times 10^4$ | $6 \times 10^4$ | $5 \times 10^4$ | $3 \times 10^4$ | $2 \times 10^3$ |
| I | $1 \times 10^4$ | $1 \times 10^4$ | $2 \times 10^4$ | $1 \times 10^4$ | $6 \times 10^3$ |
| None | $8 \times 10^7$ | $8 \times 10^7$ | $1 \times 10^8$ | $1 \times 10^8$ | $2 \times 10^7$ |

(Unit is CFU/ml)

TABLE 5

Evaluation experiment 2
Dissolved silver concentration

| Sample | First | Second | Third | Fourth | Fifth |
|---|---|---|---|---|---|
| F | 0.68 | 0.44 | 0.24 | 0.36 | 0.32 |
| G | 0.73 | 0.43 | 0.34 | 0.30 | 0.26 |
| H | 1.00 | 0.67 | 0.68 | 0.53 | 0.55 |
| I | 0.79 | 0.48 | 0.38 | 0.34 | 0.34 |
| None | 0 | 0 | 0 | 0 | 0 |

(Unit is ppm)

From the above results, the following was found.

Each sample showed an enduring bacteriostatic effect even in an artificial urine containing a plenty amount of chlorine ions which consume silver ions which are antibacterial components and a nutrient source of bacteria such as bouillon, and the like, and further a relatively high concentration of bacteria as an initial bacteria number of $10^4$ CFU/ml. The silver ion concentrations in the respective test liquids are tend to be gradually decreased by repeating 24 hours dipping but no abrupt decrease was observed.

(Evaluation Experiment 3: Copper)

To the similar ball state alumina substrate as mentioned above was coated whole surface an ammonia peptization type titanium oxide sol having an average particle size of 0.01 $\mu$m by the spray coating method, and the substrate was baked at 700° C. for one hour. Then, the substrate was dipped in a 1% by weight aqueous copper acetate solution while irradiating a BLB lamp with an ultraviolet intensity of 0.5 mW/cm$^2$ for 4 hours by rolling the sample by the shaking method whereby copper ions and metal copper were fixed thereto. Then, by ultrasonic wave washing, excess copper was removed. Thereafter, the material was washed well with water to obtain a solid material sample. The crystal type of titanium oxide fixed on the sample thus obtained was anatase. The size of the copper particle was several nm to 10 nm. As the results of observation by using a porosimeter, a large number of fine pores with an average size of 10 nm or so was observed on the surface of the sample.

As to these samples, an initial antibacterial activity, and an antibacterial activity with a repeated use were evaluated.

Here, the initial antibacterial activity was evaluated as mentioned below. As a test liquid, a bacteria solution of *Escherichia coli* (*E. coli*) or *Staphylococcus aureus* (*S. aureus*) was prepared to $10^6$ to $10^1$ CFU/ml by an artificial urine medium, and this solution was collected to a test tube with an amount of 1 ml. To the test liquid was charged one sample, and the liquid was allowed to stand at 30° C. for 18 hours. Numbers of survival bacteria at this time were evaluated. Evaluation indexes are mentioned below.

3+: Turvidity or precipitated conditions of bacteria are not changed as that of adding no antibacterial agent.

2+: Turvidity of medium is little and precipitation is admitted at the bottom of the tube.

1+: No turvidity of medium and precipitation is admitted at the bottom of the tube.

−: No precipitation and it can be concluded that no bacteria exists.

Provided that in the sample shown by −, it is unclear that bacteria are alive or not. Thus, 10 μl of the resulting reaction mixture was inoculated again to 5 ml of a new artificial urine medium and the presence or absence of growth of bacteria due to the remaining bacteria was confirmed. This evaluation indexes are shown below.

Mark *=No survival bacteria remained.

No mark=Remaining bacteria are present.

The antibacterial activity at repeated uses was evaluated as mentioned below. The similar test liquid used in the evaluation of the initial antibacterial activity was collected in a test tube in an amount of 1 ml. To the test liquid was added the sample which had been washed and sterilized by an autoclave (121° C., 20 minutes) after using it in the initial antibacterial activity evaluation, and the tube was allowed to stand again at 30° C. for 18 hours. Numbers of survival bacteria at this time were evaluated. Evaluation indexes are the same as in the initial antibacterial activity evaluation.

The evaluation results of the initial antibacterial activity and the antibacterial activity at repeated uses against *Escherichia coli* (*E. coli*) or *Staphylococcus aureus* (*S. aureus*) are shown in Table 6. As the results, in the solid material sample on which copper ions and copper are carried, it was found that it had sufficient initial antibacterial activity and antibacterial activity at repeated uses.

TABLE 6

Evaluation experiment 3 (Copper)
Antimicrobial activity test results

| Kind of bacteria | Evaluation | Initial bacteria number | | | |
|---|---|---|---|---|---|
| | | $10^6$ | $10^5$ | $10^3$ | 10 |
| Escherichia coli | Initial antimicrobial activity | — | — | — | — |
| | Repeated antimicrobial activity | — | — | —* | —* |
| Staphylococcus aureus | Initial antimicrobial activity | 1+ | — | — | — |
| | Repeated antimicrobial activity | — | —* | —* | —* |

Evaluation Experiment 4: Bath Water

To the similar ball state substrate as mentioned above was coated whole surface an ammonia peptization type titanium oxide sol having an average particle size of 0.01 μm by the spray coating method, and the substrate was baked at 700° C. for one hour. This step was repeated twice. Then, the sample was dipped in a 1% by weight aqueous silver nitrate solution while irradiating a BLB lamp for 2 hours by rolling the sample by the shaking method whereby silver ions and metal silver were fixed thereto. Then, by ultrasonic wave washing, excess silver was removed. Thereafter, the material was washed well with water to obtain a solid material sample. The crystal type of titanium oxide fixed on the sample thus obtained was anatase. Also, as the fixed silver, it was confirmed that both of 0 valence and monovalence were present.

Figure 10:
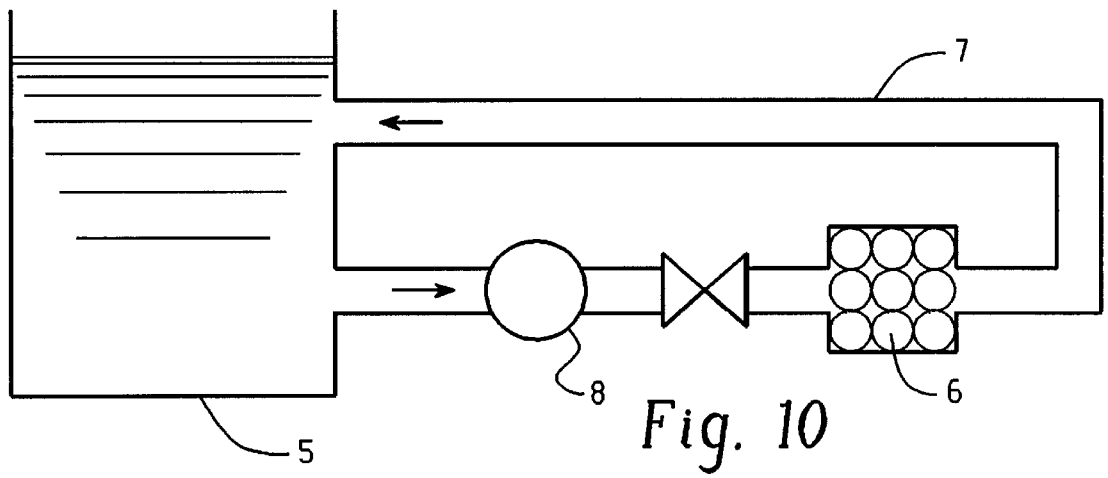
FIG. 10 is a schematic view showing a bath water circulating device of Evaluation experiment 4.

Twenty balls of the sample (antimicrobial solid material) were placed in a circulating apparatus of bath water in a public bathhouse as shown in FIG. 10, water was continuously circulated for 14 days. Changes in bath water at that time were observed.

As the results, as compared with bath water to which no antimicrobial agent is provided in the circulating apparatus, no specific difference was observed in turbidity but the following two differences were observed.

(1) In the case of bath water to which no antimicrobial agent was provided, a slime state stickiness and organic precipitates considered to be bacteria were observed in the bathtub. To the contrary, when the antimicrobial solid material was provided, no slime nor precipitates were admitted.

(2) In the case of bath water to which no antimicrobial agent was provided, it smelled a significantly strong sewage but when the antimicrobial solid material was provided, there is no sewage smell. From the results of the above trial examination, by providing the solid material at a circulating route of a storage tank such as a bathtub, pool, artificial fountain, and the like, it can be considered that these waters can be effectively purified.

Evaluation Experiment 5: Trap

To the similar ball state substrate as mentioned above was coated whole surface an ammonia peptization type titanium oxide sol having an average particle size of 0.01 μm by the spray coating method, and the substrate was baked at 700° C. for one hour. This step was repeated twice. Then, the sample was dipped in a 1% by weight aqueous silver nitrate solution while irradiating a BLB lamp for 2 hours by rolling the sample by the shaking method whereby silver ions and metal silver were fixed thereto. Then, by ultrasonic wave washing, excess silver was removed. Thereafter, the material was washed well with water to obtain a solid material sample. The crystal type of titanium oxide fixed on the sample thus obtained was anatase. Also, as the fixed silver, it was confirmed that both of 0 valence and monovalence were present.

Figure 11A:
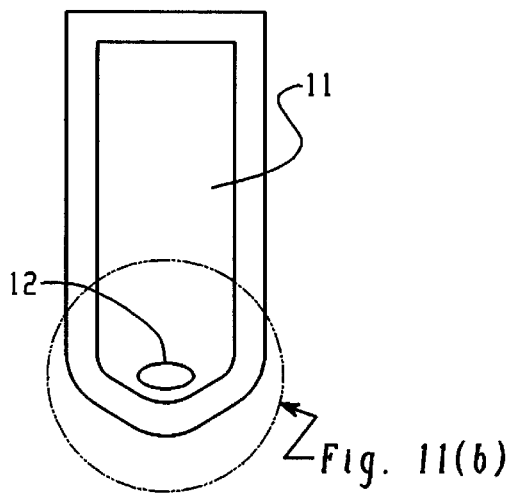
FIG. 11 is a schematic view showing a urine stool of Evaluation experiment 5.
Figure 11B:
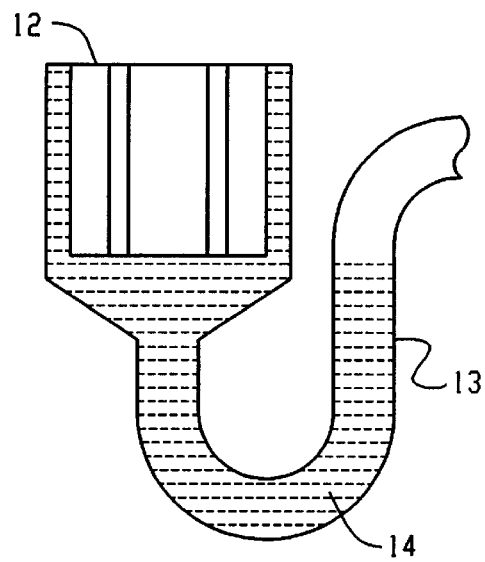

At the trap portion (see FIG. 11) of a urine stool actually used, ten solid material samples (antimicrobial solid material) as mentioned above were placed and it was allowed to stand for one month. Thereafter, dirted states of the inner wall at the trap portion and the pop-up stopper were examined. In FIG. 11, 11 is a urine stool, 12 is a pop-up stopper, 13 is a trap, and 14 is a stool residence water. As the results, the inner wall at the trap portion and the pop-up stopper of a urine stool in which no antimicrobial solid materials had been placed were changed to bright yellow, but the inner wall at the trap portion and the pop-up stopper of a urine stool in which antimicrobial solid materials had been placed were changed only to slightly yellowish whereby it was found that the antimicrobial solid materials have a remarkable effect of preventing dirt of the inner wall at the trap portion and the pop-up stopper of a urine stool.

Evaluation Experiment 6: Eluted Silver Concentration

As to the solid material Sample A used in Evaluation experiment 1, change in elution amount of silver per time was measured.

The elution amount of silver was evaluated by the method as mentioned below. Sample A was dipped in a 80 volume % ethanol for 2 hours and then dried at 50° C. for 2 hours. Ten Sample A were placed in a sterilized beaker with 200 ml of an artificial urine medium, and allowed to stand in an incubator at 30° C. for a predetermined time. Then, after filtering the artificial urine medium through a membrane filter with 0.45 μm, it was eluted out in distilled water. The silver elution amount dissolved in the distilled water was quantitatively analyzed by an atomic-absorption (Hitachi 6000 flame type). The elution amount of silver was calculated as change in a silver weight concentration in the distilled water.

Figure 12:
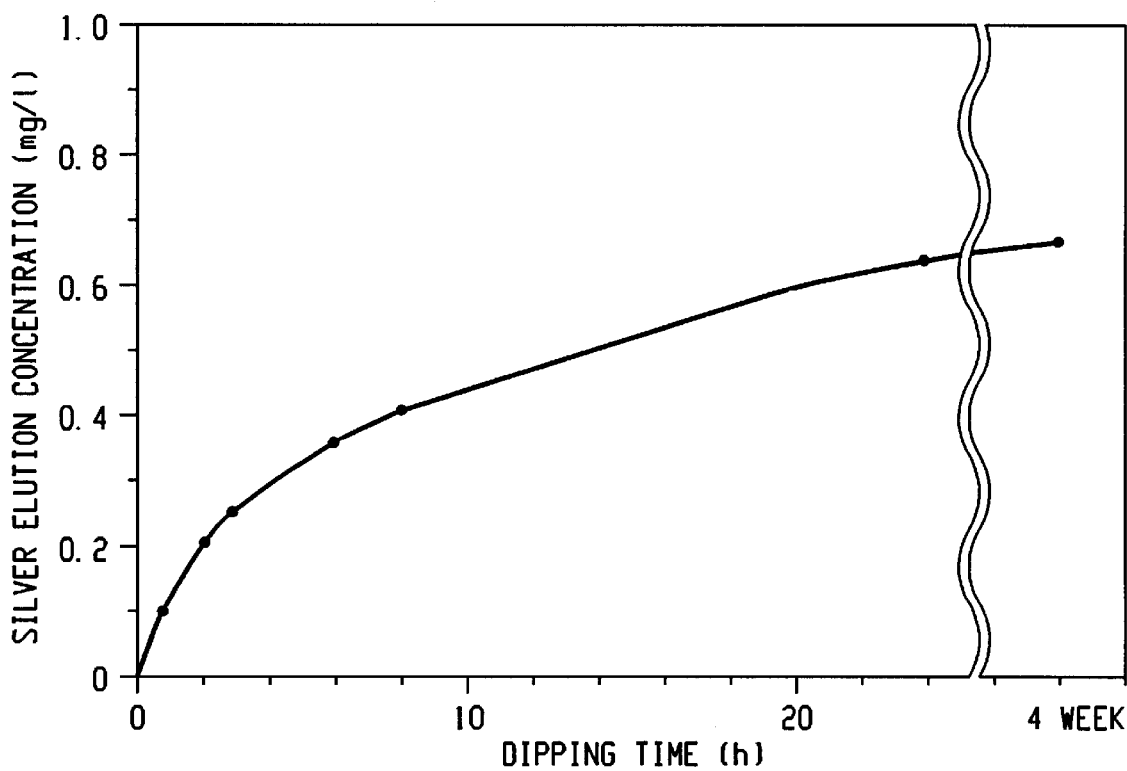
FIG. 12 is a graph showing the relationship between a dipping time in a liquid to be treated of an antimicrobial solid material and a silver ion concentration of the liquid to be treated in Evaluation experiment 6.

Change in the silver concentration is shown in FIG. 12. From the figure, it can be understood that the elution amount (inclination of a concentration line) of silver is particularly large at the initial stage. Thereafter, the silver elution concentration became substantially constant at 0.6 to 0.7 mg/liter after with the lapse of one day or so. Accordingly, when the silver ions are released with a certain amount in a solution, it can be understood that a mechanism of inhibiting release of silver ions works. In Evaluation experiment 1, the antimicrobial activity of the present sample was maintained for one month so that, in collected water, if the silver elution concentration is maintained with such a degree, it can be considered that the antimicrobial activity can be maintained for a significantly long term.

Next, the samples once carried out the above experiment were recovered, and after dipping in a 80% by volume of ethanol for 2 hours, these were dried at 50° C. for 2 hours. Ten Sample A were placed in a sterilized beaker with 200 ml of an artificial urine medium, and allowed to stand in an incubator at 30° C. for a predetermined time. This test was repeated for several times.

Figure 13:
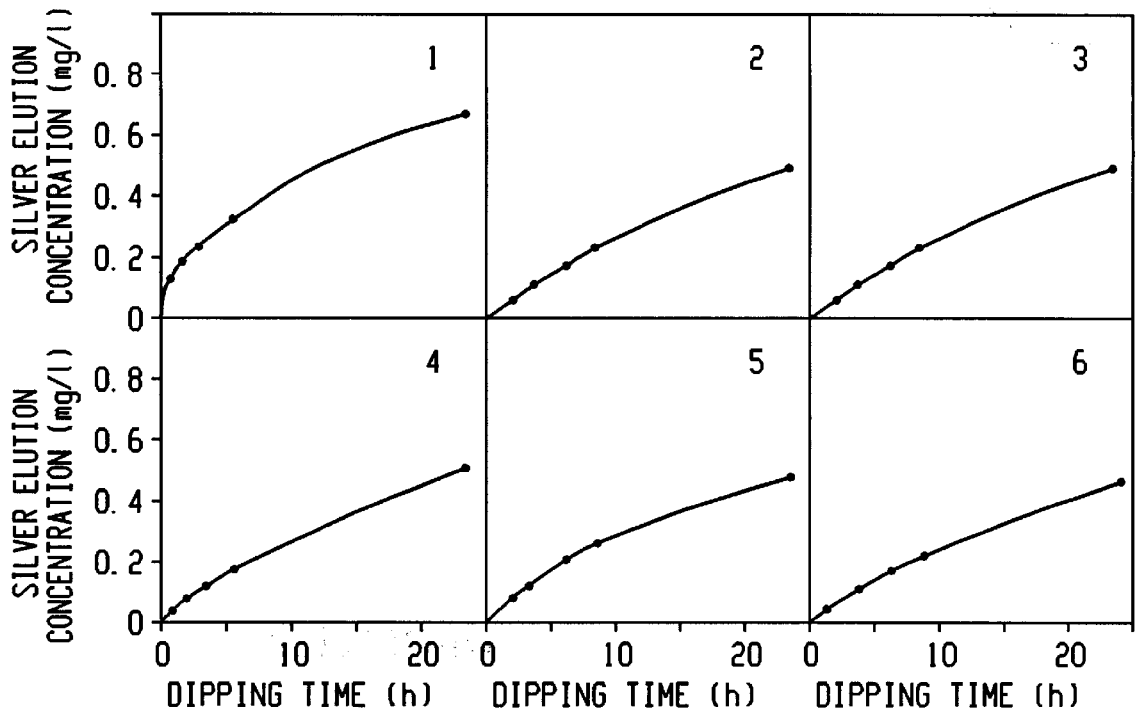
FIG. 13 is a similar graph as in FIG. 12 in repeated soaking test in Evaluation experiment 6.

The results are shown in FIG. 13. From the figure, it seems that the silver elution amount at the first time is larger than the others, it can be considered by the effect of silver ions attached to the surface of the solid material sample. Thereafter, the curve showing change in the silver elution concentration with a lapse of time showed the similar tendency from the second time to the sixth time. It was found that the tendency that the concentration after the lapse of one day or so becomes substantially constant at 0.4 to 0.6 mg/liter was repeated. Accordingly, it can be understood that when the silver ion concentration in the solution becomes 0, a mechanism of releasing silver ions in the solution again with a constant amount and, when the constant amount is released, inhibiting release of silver ions works. This mechanism can be said to be a mechanism of automatically adjusting the silver elution concentration or a mechanism of automatically controlling the release amount of silver ions.

This tendency is explained as mentioned below.

In the solid material Sample A prepared in Evaluation experiment 1, silver ions are supported in the porous alumina substrate, the porous anatase type titanium oxide particle (average crystallite size 10~40 nm) layer is formed on the surface thereof, and between gaps of the titanium oxide particles, metal state silver particles (average particle size 1~10 nm) are fixed by the photocatalytic function of said titanium oxide particles. On the surface thereof, a little amount of silver ions excessively carried thereon is present. The silver ions are fixed while maintaining its electrical neutrality with the anion such as nitrate ions, and the like.

With a lapse of time, pores existing at the surface of Sample A are covered by silver particles deposited by photoreduction so that elution of silver ions supported at the porous portion of the substrate is inhibited. This silver deposition reaction is a deposition reaction of silver ions and is in equilibrium relation with the elution reaction of metal silver in the solution which is a reverse reaction. Thus, when the silver elution concentration in the solution reaches to 0.1 to 1 ppm (a concentration sufficient for antimicrobial effect), the above equilibrium is realized and the system becomes the state that silver ions are apparently not eluted in the solution. However, at the time of next use, the silver elution concentration in the solution at the initial stage becomes 0 so that elution occurs again and continues until the silver elution concentration in the solution reaches to 0.1 to 1 ppm. In this manner, it can be considered that the silver elution amount per one use can be saved so that it endures plural times of uses.

In order to clarify the mechanism, in Evaluation experiment 14 mentioned hereinbelow, change of a tendency in the silver elution amount in relation to a soaking time was observed by changing an intensity of ultraviolet ray irradiated to a solid material at the time of soaking the solid material sample.

Evaluation Experiment 7: Silver Elution Concentration

Silver nitrate was dissolved in super pure water to prepare a solution of 100 mg/liter in terms of a silver mount. This solution was diluted with an artificial urine to prepare several kinds of media having different silver concentrations. To 2 ml of the respective media was added 0.1 ml of a bacterial suspension of Escherichia coli (E. coli) to make a final bacterial concentration of $10^5$ CFU/ml. Then, the respective media were placed in an incubator at 30° C. for 18 hours and silver reacted on the bacteria. Thereafter, 1 g/liter of an aqueous potassium iodide solution was added to the respective media to precipitate and recover the silver as silver iodide, and then the number of survival bacteria after the test was measured.

Figure 14:
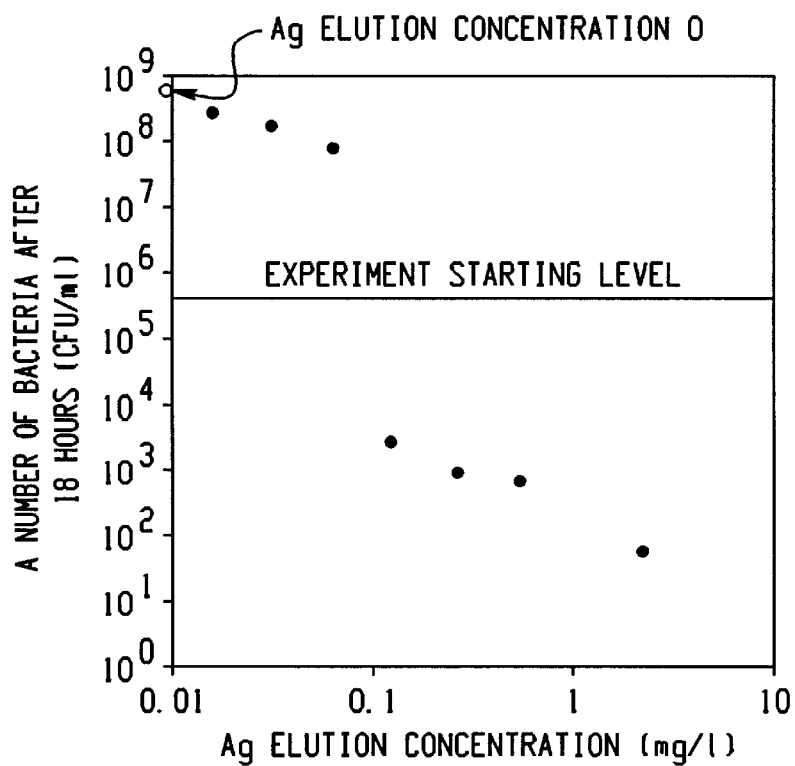
FIG. 14 is a graph showing the relationship between an Ag ion concentration in a medium and a number of bacteria after 18 hours in Evaluation experiment 7.

FIG. 14 is a graph showing the relationship between the silver concentration and the number of survival bacteria. From this graph, it was found that, when the silver concentration in the solution became 0.1 mg/liter or more, sufficient antibacterial effect appeared even when in a solution system containing much amount of chlorine ions (0.17 mol/liter) like an artificial urine.

On the other hand, after the solid material Samples A, C, D and E in Evaluation experiment 1 were dipped in 2 liters of an artificial urine for 4 weeks, the silver elution concentrations when they were dipped again in an artificial urine for 18 hours were measured. The results are shown in Table 7. In Samples C, D and E, the silver elution amounts did not reach to 0.1 mg/liter. Thus, it can be considered that, in Evaluation experiment 1, no antibacterial effect was admitted in Samples C, D and E after use for a long term. To the contrary, in Sample A, the silver elution concentration is 0.1 mg/liter or more, and thus, it can sufficiently cope with the situation (use) of such a high chlorine ion concentration and endure plural times of uses.

TABLE 7

Results of Evaluation experiment 7

| Sample | Silver elution concentration (mg/l) |
| --- | --- |
| A | 0.68 ~ 0.46 (*1) |
| B | 0.04 |
| D | 0.03 |
| E | 0.03 |

(*1) 0.46 is a value when the sample which is used in plural times used test (Evaluation experiment 6) is used.

Evaluation Experiment 8: Change in Baking Temperature

The similar rod substrate as that used in Evaluation experiment 2 was coated on the whole surface thereof a titanium oxide sol by dipping it in an ammonia peptization type titanium oxide sol having an average diameter of 0.01 μm, and then, the sample was baked at 650° C., 700° C., 750° C. and 800° C. for one hour. Then, the respective samples were dipped in 1% by weight of an aqueous silver nitrate solution while irradiating a BLB lamp for 2 hours to support and fix silver ions and metal silver. Then, by ultrasonic wave washing, excess silver was removed, and thereafter, the respective samples were washed with water well and dried to obtain solid material Samples O, P, Q and R. The crystal type of the titanium oxide fixed on the obtained solid materials was an anatase. The size of the silver particles was several nm to 10 nm. By the observation using a porosimeter, fine pores having an average diameter of 10 nm or so were observed at the surface of the solid materials.

With respect to the obtained samples, an average crystallite size of titanium oxide and a silver elution amount after repeated uses were examined. The average crystallite size of titanium oxide was measured by powder X-ray diffraction. The silver elution amount after repeated uses was measured by repeating, for three times, the step of allowing the sample to stand in 100 ml of distilled water for 24 hours, then the sample was transferred to 100 ml of fresh distilled water and allowed to stand for 24 hours, and analyzing the silver amount in the distilled water after allowing to stand for 24 hours at the third time by an atomic-absorption.

The results are shown in Table 8. From the table, accompanying with increase in baking temperature of titanium oxide, the average crystallite size of titanium oxide became 10 nm to 40 nm, but the silver elution amounts were each within the range of 0.1 to 1 mg/liter in each temperature and good results were shown.

TABLE 8

Results of Evaluation experiment 8

| Sample | Baking temperature (° C.) | Average crystallite size (nm) | Silver elution concentration (mg/l) |
|---|---|---|---|
| O | 650 | 12 | 0.80 |
| P | 700 | 15 | 0.70 |
| Q | 750 | 20 | 0.75 |
| R | 800 | 40 | 0.70 |

Evaluation Experiment 9: Change in Sol Dipping Time

Samples were prepared in the same manner as in Sample A except for controlling the dipping time of the titanium oxide sol from 2 seconds to one hour, and a carried amount of titanium oxide per unit area and a silver elution amount after repeated uses were examined. The carried amount of titanium oxide per unit area was calculated by obtaining the difference between the substrate weight after coating and baking the titanium oxide sol and the weight of the substrate before coating the titanium oxide sol, and dividing the weight difference by the surface area of the substrate. The silver elution amount after repeated uses was evaluated by the same method as in the above mentioned Evaluation experiment 8.

The results are shown in Table 9. From the table, accompanying with increase in the dipping time of the substrate in the titanium oxide sol, the carried amount of titanium oxide per unit area increased but the silver elution amount (silver elution concentration) after repeated uses at this time was not substantially affected thereby, and even at 15 mg/cm$^2$ or so, it was sufficient as 0.4 to 0.6 mg/liter.

TABLE 9

Results of Evaluation experiment 9

| Titanium oxide sol dipping time | Titanium oxide carried amount (mg/cm$^2$) | Silver elution amount (mg/l) |
|---|---|---|
| 2 seconds | 15 | 0.60 |
| 5 seconds | 18 | 0.63 |
| 10 seconds | 15 | 0.55 |
| 30 seconds | 16 | 0.45 |
| 1 minute | 17 | 0.55 |

TABLE 9-continued

Results of Evaluation experiment 9

| Titanium oxide sol dipping time | Titanium oxide carried amount (mg/cm$^2$) | Silver elution amount (mg/l) |
|---|---|---|
| 2 minutes | 19 | 0.55 |
| 5 minutes | 22 | 0.58 |
| 10 minutes | 23 | 0.60 |
| 30 minutes | 28 | 0.55 |
| 1 hour | 28 | 0.55 |

Evaluation Experiment 10: Change in Silver Nitrate Concentration

Samples were prepared in the same manner as in Sample A except for changing the concentration of the aqueous silver nitrate solution as mentioned below. As to the obtained samples, a silver elution amount after repeated uses was examined. The silver elution amount after repeated uses was evaluated by the same method as in Evaluation experiment 8.

Figure 15:
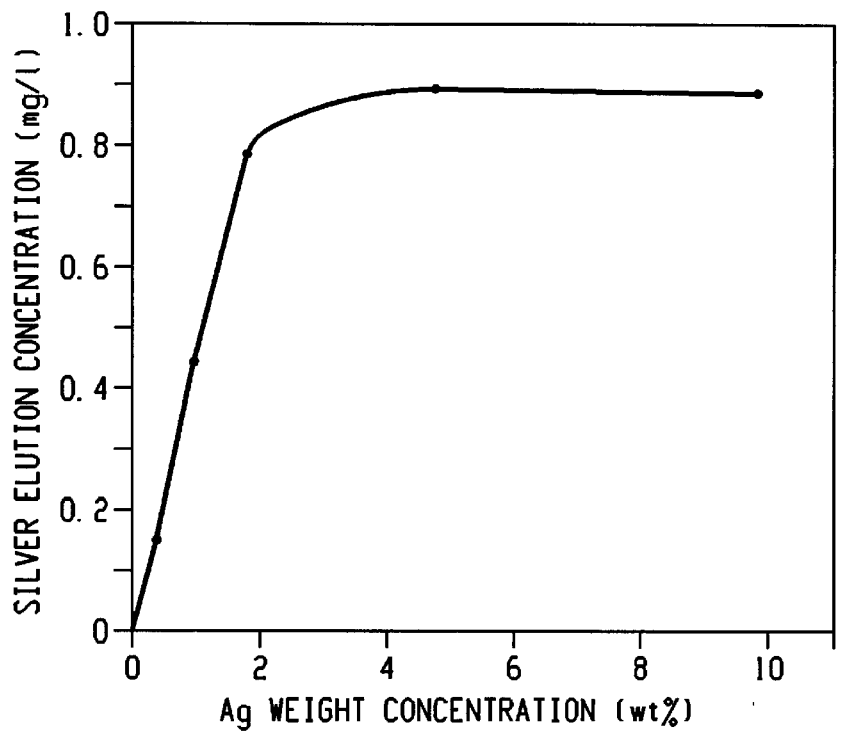
FIG. 15 is a graph showing the relationship between a silver weight concentration in an aqueous silver nitrate solution and a silver ion concentration in a liquid to be treated to which an antimicrobial solid material is dipped.

The graph of the experimental results is shown in FIG. 15. From the graph, it can be understood that up to 5% by weight of the silver weight concentration in the aqueous silver nitrate solution, the silver elution concentration (silver elution amount) after repeated uses also increases accompanied with increase in the silver weight concentration. However, the silver weight concentration is raised than the above, the silver elution concentration becomes constant. Also, the silver elution concentration after repeated uses became 0.1 mg/liter or more when the silver weight concentration in the aqueous silver nitrate solution was made 0.3% by weight or more, so that the solid material had a sufficient antimicrobial activity.

Here, the reason why the system becomes the silver elution amount having a sufficient antimicrobial activity when the silver weight concentration in the aqueous silver nitrate solution is made 0.3% by weight or more is considered that a sufficient amount of silver elution is supported in the porous substrate and the photocatalytic layer.

Evaluation Experiment 11: Change in Silver Nitrate Dipping Time

Samples were prepared in the same manner as in Sample A except for changing the dipping time to the aqueous silver nitrate solution within the range of 2 seconds to 1 hour, and a silver elution amount after repeated uses was examined. The silver elution amount after repeated uses was evaluated by the same method as described in the above Evaluation experiment 8.

Figure 16:
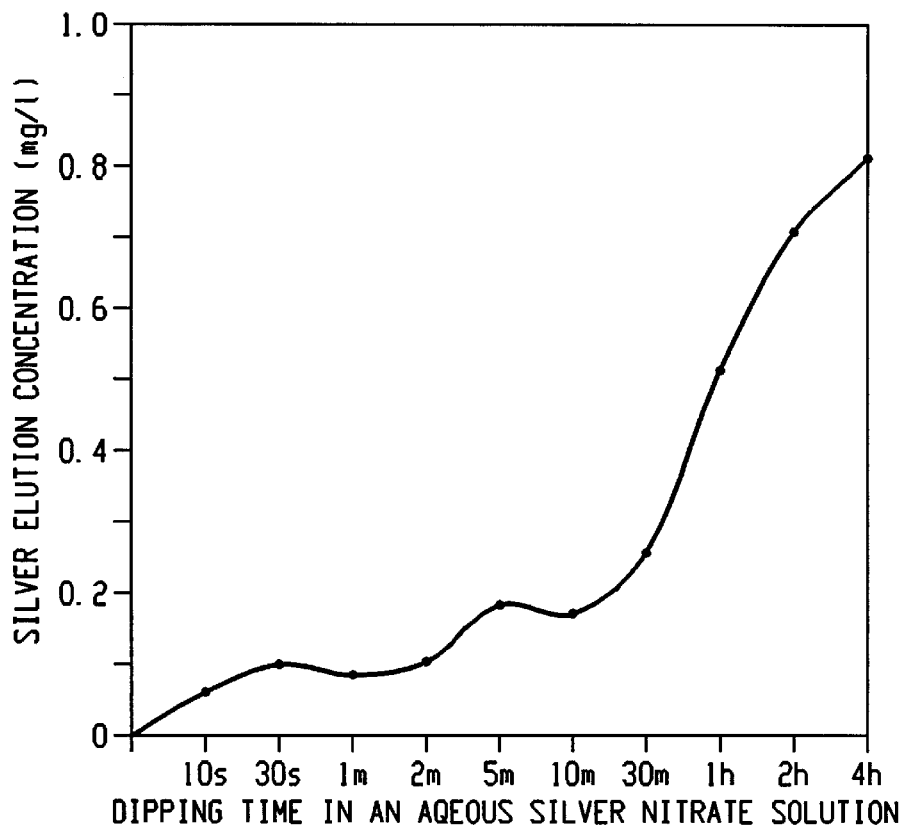
FIG. 16 is a graph showing the relationship between a dipping time in an aqueous silver nitrate solution and a silver ion concentration in a liquid to be treated to which an antimicrobial solid material is dipped in Evaluation experiment 11.

The graph of the experimental results is shown in FIG. 16. From the graph, it can be understood that the silver elution amount after repeated uses increases accompanied with increase in the dipping time, and when the time exceeds 2 minutes, the silver elution amount after repeated uses becomes 0.1 mg/liter or more whereby sufficient antimicrobial activity was exhibited. Here, the reason why the silver elution amount becomes an amount showing a sufficient antimicrobial activity when the dipping time is made 2 minutes or longer is considered that a sufficient amount of silver elution is supported in the porous substrate and the photocatalytic layer.

Evaluation Experiment 12: Comparison of Silver and Copper

According to the same method as in the method of obtaining Sample A, a silver carried solid material Sample S was obtained.

On the other hand, according to the same method as in Evaluation experiment 3, a copper carried solid material Sample T was obtained.

As to the obtained Samples S and T, an effect on fungus, and an effect on bacteria were examined.

The effect on fungus was evaluated as mentioned below. Candida (*C. albicans*) which is fungus had been adjusted to $10^7$ to $10^1$ CFU/ml in a bouillon medium containing 0.9% of glucose was collected in a test tube in an amount of 1 ml, and one antimicrobial agent sample was placed therein and allowed to stand at 30° C. for 18 hours. A survival ratio of fungi at this time was evaluated. Evaluation indexes are shown below.

3+: Turvidity or precipitated conditions of microorganisms are not changed as that of adding no antimicrobial agent.

2+: Turvidity of medium is little and precipitation is admitted at the bottom of the tube.

1+: No turvidity of medium and precipitation is admitted at the bottom of the tube.

−: No precipitation and it can be concluded that no microorganisms exists.

Provided that in the sample shown by −, it is unclear that microorganisms are alive or not. Thus, 10 μl of the resulting reaction mixture was inoculated again to 5 ml of a new artificial urine medium and the presence or absence of growth of microorganisms due to the remaining microorganisms was confirmed. This evaluation indexes are shown below.

Mark *=No survival microorganisms remained.

No mark=Remaining microorganisms are present.

The effect on microorganisms was evaluated as mentioned below. A microorganism solution of *S. marcescens* was adjusted to $10^7$ to $10^1$ CFU/ml in an artificial urine medium was innoculated in a test tube in an amount of 1 ml, and one antimicrobial agent sample was placed therein and allowed to stand at 30 ° C. for 18 hours. A survival ratio of microorganisms at this time was evaluated. Evaluation indexes are made the same as in the case of the above-mentioned fungus.

The experimental results about the fungus are shown in Table 10. As can be seen from Table 10, both of Samples S and T showed excellent antifungal activities of—at the fungus concentration of $10^3$ CFU/ml or less. Also, when Samples S and T are compared, the solid material T on which copper is carried showed more excellent characteristics against fungus.

TABLE 10

Results of Evaluation experiment 12 (fungus)

| Initial fungus concentration (CFU/ml) | $10^7$ | $10^6$ | $10^5$ | $10^4$ | $10^3$ | $10^1$ |
|---|---|---|---|---|---|---|
| Sample S (silver type) | 2+ | 1+ | 1+ | 1+ | —* | —* |
| Sample T (copper type) | 2+ | 1+ | 1+ | —* | —* | —* |

The experimental results about the bacteria are shown in Table 11. As can be seen from Table 11, both of Samples S and T showed excellent antimicrobial activities of—at the bacteria concentration of $10^5$ CFU/ml or less. Also, when Samples S and T are compared, the solid material S on which silver is carried showed more excellent characteristics against bacteria.

From the above matter, it can be considered that in the above-mentioned solid material, both of silver and copper are suppoeted, it becomes a solid material having both of antibacterial activity and antifungal activity.

TABLE 11

Results of Evaluation experiment 12 (bacteria)

| Initial bacteria concentration (CFU/ml) | $10^7$ | $10^6$ | $10^5$ | $10^3$ | $10^1$ |
|---|---|---|---|---|---|
| Sample S (silver type) | 1+ | —* | —* | —* | —* |
| Sample T (copper type) | 1+ | 1+ | —* | —* | —* |

Evaluation Experiment 13 (Effects on Bath Water)

To a porous alumina substrate with a 5 mmΦ ball state having an open porosity of 62% by volume was coated the whole surface with an ammonia peptization type titanium oxide sol having an average particle size of 0.01 μm by the spray coating method, and the substrate was baked at 700° C. for one hour. This step was repeated twice. Then, the sample was dipped in a 1% by weight aqueous silver nitrate solution while irradiating a BLB lamp for 2 hours by rolling the sample by the shaking method to support silver thereto. Then, by applying ultrasonic wave, excess silver was removed. Thereafter, the sample was washed well with water to obtain a solid material Sample A. The crystal type of titanium oxide fixed on the resulting solid material was anatase. The size of the silver particles was several nm to 10 nm. In the solid material, fine pores having an average of 10 nm or so were observed by a porosimeter with a large number. It was confirmed that in the supported silvers, both of 0 valence and monovalence existed.

As to these Samples, the initial antibacterial activity and the antimicrobial activity after long term use were evaluated.

The initial antibacterial activity was evaluated as mentioned below. First, a solid material sample was dipped in a 80% by volume ethanol for 2 hours, then dried it at 50° C. and the surface was washed. Then, a bacterial suspension of *Escherichia coli* (*E. coli*) was innoculated in an amount of $10^5$ CFU in an artificial urine (its composition was shown in Table 1), 10 solid material samples were placed therein, and after allowing the mixture to stand in an incubator at 30° C. for 24 hours, the number of bacteria was measured.

The antibacterial activity at repeated uses was evaluated as mentioned below. First, a solid material sample was dipped in a 80% by volume ethanol for 2 hours, then dried at 50° C. and the surface was washed. Next, to a sterilized beaker were added 2 liters of the artificial urine and the ten solid material samples, and it was allowed to stand for one month. Thereafter, the solid materials were taken out, sterilized in an autoclave at 121° C. for 20 minutes, dipped in a 80% by volume ethanol for 2 hours, and then, dried at 50° C. and the surface was washed. Then, a bacteria solution of *Escherichia coli* (*E. coli*) was innoculated in an amount of $10^5$ CFU in an artificial urine (its composition was shown in Table 1), 10 solid material samples were placed therein, and after allowing the mixture to stand in an incubator at 30° C. for 24 hours, the number of bacteria was measured.

Figure 9:
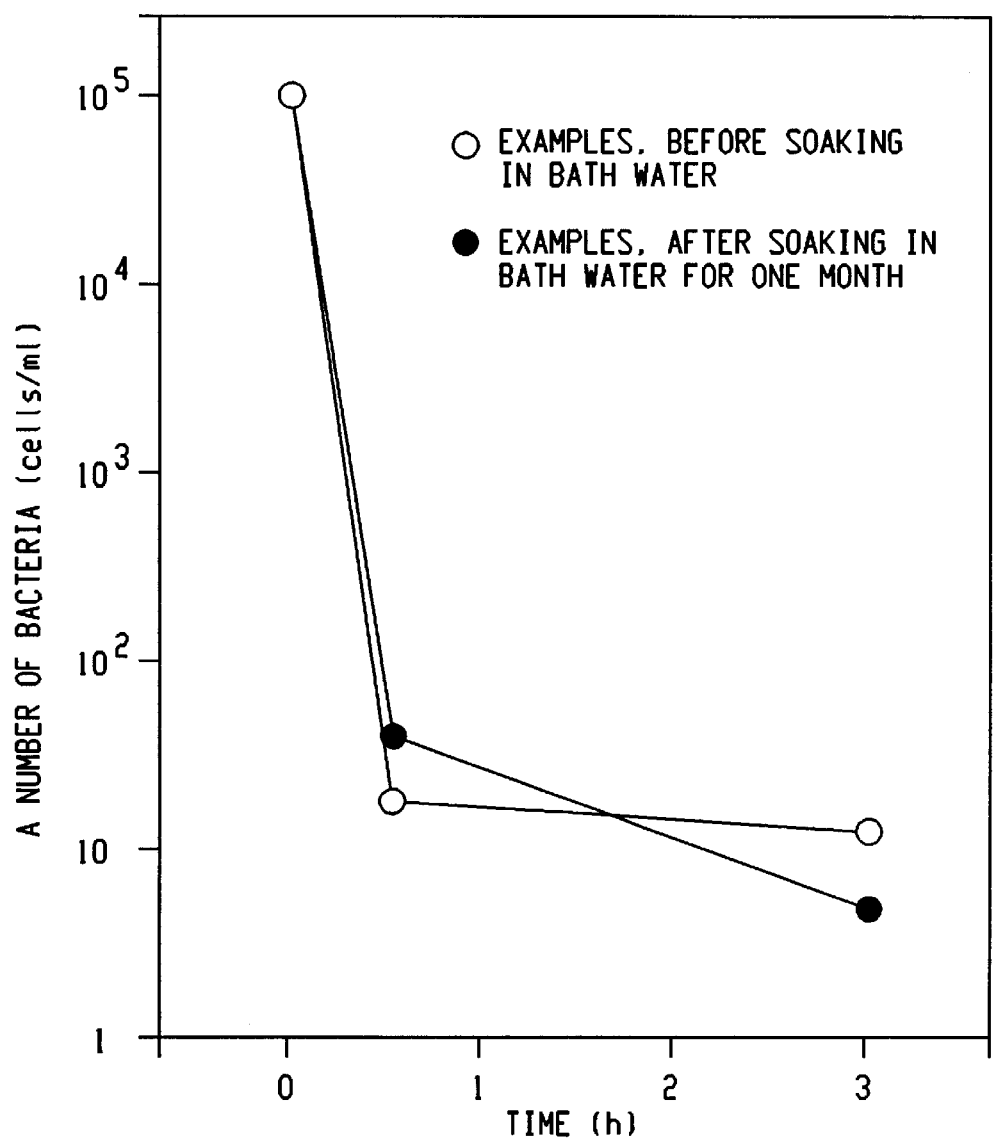
FIG. 9 is a graph showing the relationship between a time before and after soaking in bath water for one month and a number of bacteria in Evaluation experiment 13.

The results of the initial antibacterial activity and the antibacterial activity at repeated uses are each shown in FIG. 9. In either of the evaluation, the number of survival bacteria was decreased to 10 CFU or less and excellent bactericidal activities were shown. Accordingly, it was found that the sample of the present invention had effects not only on the polyion solution such as the artificial urine but also a bath water.

Evaluation Experiment 14

As described in Evaluation experiment 6, in the antimicrobial solid material according to the present invention, when the silver ion concentration in the solution at the repeated uses is made 0, a mechanism of releasing silver ions in the solution again with a necessary amount and, when the necessary amount is released, inhibiting release of the antimicrobial component works. And the reason is considered that equilibrium between the silver deposition reaction due to photoreduction and the elution reaction of metal silver into the solution is established when the silver ion concentration in the solution reaches to a certain value.

In order to clarify the mechanism, by changing an intensity of the ultraviolet ray irradiating to a solid material when the solid material sample is dipped, changes in a tendency of the silver elution amount to the dipping time was observed.

Figure 19:
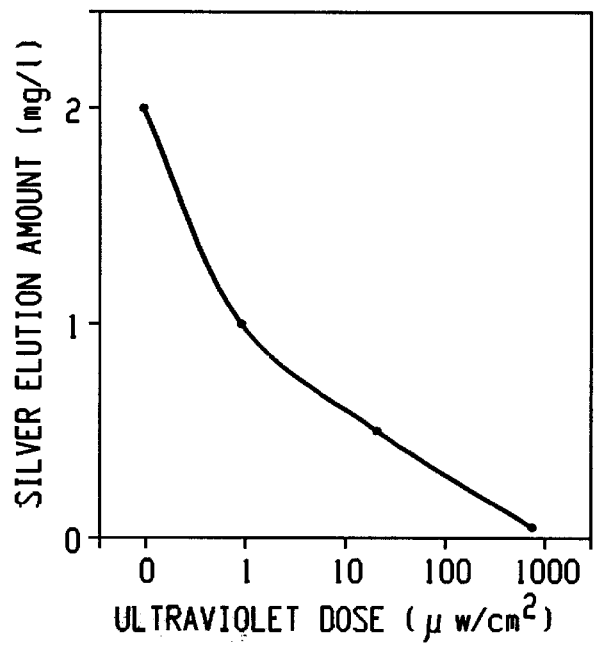
FIG. 19 is a graph showing the relationship between an ultraviolet dose and a silver elution amount in Evaluation experiment 14.

While dipping the sample used in Experiment 6 in pure water in a beaker, light different in an intensity of ultraviolet ray was irradiated from upper portion, and the silver elution amount after dipping for 24 hours was measured. The results are shown in FIG. 19. As the results, whereas at the ultraviolet ray intensity of 0 $\mu W/cm^2$, the silver elution amount was 2 mg/liter, at 1 $\mu W/cm^2$, it was 1 mg/liter, at 20 $\mu W/cm^2$, it was 0.5 mg/liter, and at 500 $\mu W/cm^2$, it was 0.03 mg/liter. Thus, it was confirmed the tendency that the ultraviolet ray intensity is larger, the elution amount becomes small. This can be considered that, when the ultraviolet ray intensity is large, the silver deposition reaction due to photoreduction more proceeds whereby the above equilibrium shifts to the direction of a high deposition concentration, i.e., the direction of a low elution concentration.

Further, by changing the intensity of ultraviolet ray, it is possible to change the silver elution amount.

For example, from the above results, at the room illumination (usual ultraviolet ray intensity: 1 to 100 $\mu W/cm^2$) or so, the elution amount becomes 0.1 to 1 mg/liter so that a sufficient antimicrobial activity is shown in a nontreated solution containing many ions such as an artificial urine and a used silver amount can be saved.

Also, as shown in Table 12, in ultrapure water, a sufficient antimicrobial activity can be obtained even when the silver concentration in the solution is 1 $\mu g$/liter or so. The results of Table 12 were obtained as mentioned below. First, after dissolving silver nitrate in ultrapure water with a predetermined concentration, a bacterial suspension of *Escherichia coli* (*E. coli*) was added and the final bacterial concentration was made to be $2 \times 10^5$ CFU/ml. Thereafter, silver was reacted on the bacteria in an incubator at 30° C. for 2 hours. Then, 1 g/liter of an aqueous potassium iodide solution was added thereto to recover silver as silver iodide by precipitation. Then, the number of survival bacteria after the test was measured and the number of survival bacteria based on the silver ion concentration in the solution was calculated. Accordingly, in a liquid to be treated in which an amount of ions in the solution is little as in the ultrapure water, when irradiation is carried out with a light source (a metal halide lamp, BLB lamp, halogen lamp, xenone lamp, mercury lamp, and the like) having a more strong intensity of ultraviolet ray, the used silver amount can be further saved.

TABLE 12

Results of Evaluation experiment 14

| Solvent | Initial bacteria concentration (CFU/ml) | Silver dissolution concentration (mg/liter) | Reaction time (h) | Survival bacteria number (CFU/ml) |
| --- | --- | --- | --- | --- |
| Well water (Cl⁻) = $1.5 \times 10^3$ mol/liter | $2.2 \times 10^5$ | 0<br>0.001<br>0.005<br>0.01<br>0.1 | 2 | $1.8 \times 10^5$<br>$4.2 \times 10^4$<br>$4.0 \times 10^0$<br>0<br>0 |

TABLE 12-continued

Results of Evaluation experiment 14

| Solvent | Initial bacteria concentration (CFU/ml) | Silver dissolution concentration (mg/liter) | Reaction time (h) | Survival bacteria number (CFU/ml) |
| --- | --- | --- | --- | --- |
| Ultrapure water | $2.2 \times 10^5$ | 0<br>0.001<br>0.005<br>0.01 | 2 | $2.1 \times 10^5$<br>$2.2 \times 10^2$<br>$1.1 \times 10^1$<br>$1.0 \times 10^0$ |

Also, for comparison, 5 g of a silver ion-supported zeolite was dipped in 500 ml of a PBS (a solution in which 0.8% sodium chloride was added to 10 mmol/liter of a $Na_2HPO_4$—$NaH_2PO_4$ buffer with a pH of 7) for 16 hours (a silver supported amount corresponds to 300 ml/liter). As the results, in the silver ion-supported zeolite which is a conventional silver ion-supported solid material, the result was 264 mg/liter whereby almost all silver ions are released in a liquid to be treated containing many ions such as a PBS. To the contrary, in the solid material of the present invention, only 2 mg/liter or so was released when it was soaked for 24 hours at a dark time. Thus, it can be found that the material shows sufficient antimicrobial activity and also the used silver amount can be saved.

Evaluation Experiment 15: Test of Uses for Plural Times by Dipping in Bath Water In a conical flask was charged 200 ml of a bath water to which $10^5$ CFU of a bacterial suspension of *Escherichia coli* (*E. coli*) was added. Ten solid material samples prepared in the same manner as in Evaluation experiment 13 were soaked therein and the flask was allowed to stand in an incubator at 30° C. for 24 hours, and then the antimicrobial activity was firstly examined. Thereafter, the bath water was replaced, and the samples previously dipped were again soaked in 200 ml of the newly added bath water to which $10^5$ CFU of a bacterial suspension of *Escherichia coli* (*E. coli*) was added. Then, the antimicrobial activity thereafter was examined and the procedure was repeated.

Also, for comparison, the same test was carried out for the same volume of various silver carriers as the solid material sample.

Figure 20:
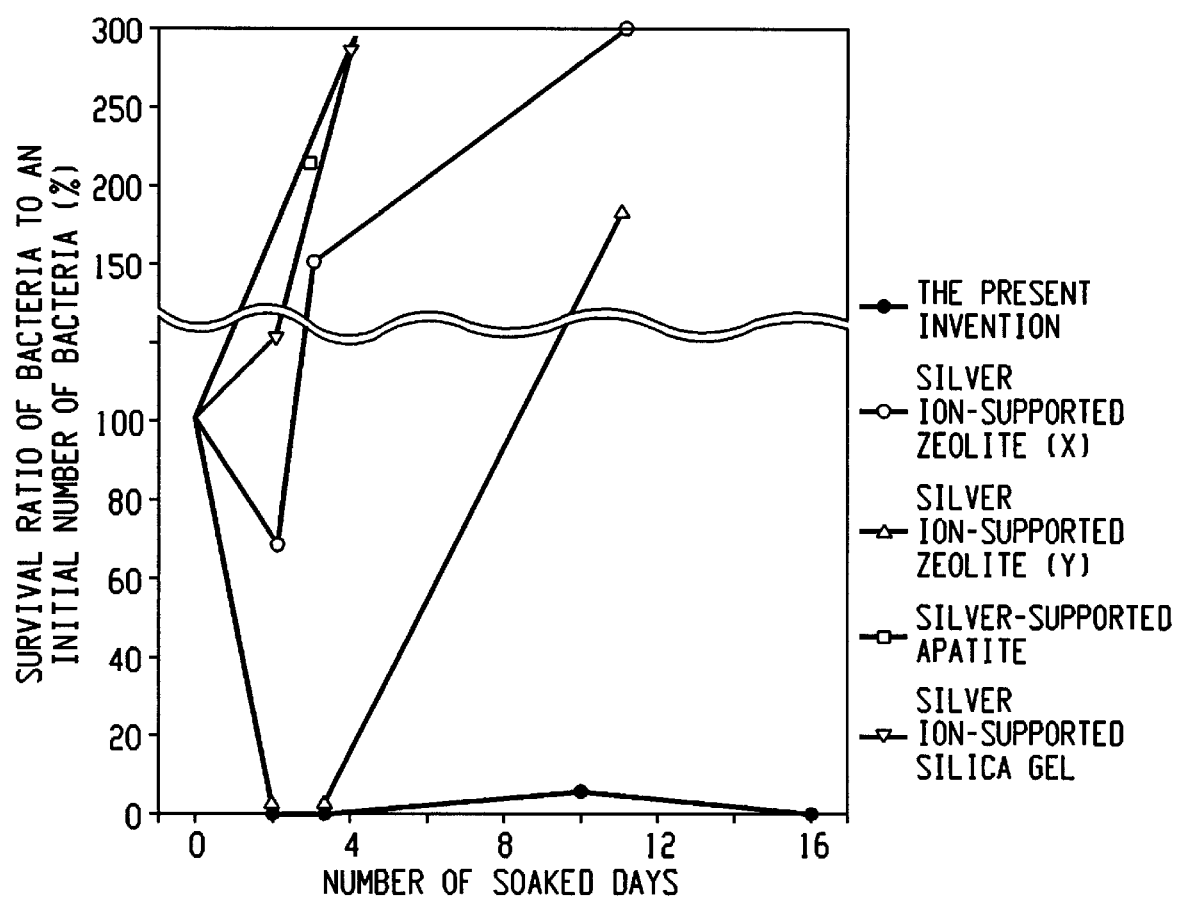
FIG. 20 is a graph showing the relationship between a number of soaked days to a liquid to be treated of an antimicrobial solid material and a survival ratio of bacteria to an initial number of bacteria in the liquid to be treated in Evaluation experiment 15.

The results are shown in FIG. 20. From the figure, in the silver ion supported type silver ion-supported zeolite, silver ion-supported silica gel, and metal silver supported type silver-supported apatite, the bacteriostatic activities were lost within 10 days or so, but in the solid material of the present invention, it was found that after at least 15 days are lapsed, it had a sufficient antimicrobial activity.

EFFECTS OF THE INVENTION

The antimicrobial solid material of the present invention has both of the initially effective antimicrobial agent and enduringly effective antimicrobial agent so that a sufficient antimicrobial activity can be maintained for a long term against various forms of sewages such as circulating water, collected water and flowing water and the contacting portion thereof.

We claim:

1. An antimicrobial solid material which comprises (1) metal ions selected from the group consisting of silver ions, copper ions and zinc ions, as antimicrobial metal ions; and (2) a metal selected from the group consisting of silver, copper and zinc, as an antimicrobial metal in a metal state.

2. An antimicrobial solid material which comprises a mixed layer having (1) metal ions selected from the group consisting of silver ions, copper ions and zinc ions, as antimicrobial metal ions, and (2) a metal selected from the group consisting of silver, copper and zinc, as an antimicrobial metal in a metal state.

3. An antimicrobial solid material which comprises (1) metal ions selected from the group consisting of silver ions, copper ions and zinc ions, as antimicrobial metal ions, and (2) a metal selected from the group consisting of silver, copper and zinc, as an antimicrobial metal in a metal state, said antimicrobial solid material being supported on a substrate.

4. An antimicrobial solid material which comprises a mixed layer having (1) metal ions selected from the group consisting of silver ions, copper ions and zinc ions, as antimicrobial metal ions, and (2) a metal selected from the group consisting of silver, copper and zinc, as an antimicrobial metal in a metal state, said mixed layer being supported on a substrate.

5. An antimicrobial solid material which comprises:
a substrate,
an antimicrobial metal ion layer comprising metal ions selected from the group consisting of silver ions, copper ions and zinc ions, said antimicrobial metal ion layer being fixed on said substrate, and
an antimicrobial metal layer in a metal state comprising a metal selected from the group consisting of silver, copper and zinc, said antimicrobial metal layer being fixed on said antimicrobial metal ion layer and is being permeable to said antimicrobial metal ions.

6. An antimicrobial solid material which comprises:
a substrate,
an antimicrobial metal ion layer comprising metal ions selected from the group consisting of silver ions, copper ions, and zinc ions, fixed on said substrate, and
a mixed layer having (1) metal ions selected from the group consisting of silver ions, copper ions and zinc ions, as antimicrobial metal ions, and (2) a metal selected from the group consisting of silver, copper and zinc, as an antimicrobial metal in a metal state, said mixed layer being fixed on said antimicrobial metal ion layer.

7. An antimicrobial solid material which comprises:
a substrate,
an antimicrobial metal ion layer comprising metal ions selected from the group consisting of silver ions, copper ions and zinc ions, fixed on said substrate, and
an ion release-suppressing layer comprising particles of photocatalyst and metal in a metal state, through which said antimicrobial metal ions fixed to part of gaps between said particles are permeable, said ion release-suppressing layer being fixed on said antimicrobial metal ion layer and inhibiting elution of said metal ions.

8. An antimicrobial solid material which comprises:
a substrate,
an antimicrobial metal ion layer comprising metal ions selected from the group consisting of silver ions, copper ions and zinc ions, fixed on said substrate, and
an ion release-suppressing layer comprising (1) metal ions selected from the group consisting of silver ions, copper ions and zinc ions, as antimicrobial metal ions, (2) particles of photocatalyst and (3) an antimicrobial metal in a metal state, through which said antimicrobial metal ions fixed to part of gaps between said particles are permeable, said ion release-suppressing layer being fixed on said antimicrobial metal ion layer.

9. The antimicrobial solid material according to claim 7 or 8, wherein said ion release-suppressing layer has a function of controlling elution of the antimicrobial metal ions from said antimicrobial metal ion layer by controlling separating of the antimicrobial metal at the surface of said ion release-suppressing layer by irradiating light containing an ultraviolet ray to said photocatalyst when said antimicrobial solid material is to be used in a liquid.

10. An antimicrobial solid material which comprises:
a substrate,
an antimicrobial metal ion layer comprising metal ions selected from the group consisting of silver ions, copper ions and zinc ions, fixed on said substrate,
a photocatalyst layer fixed on said antimicrobial metal ion layer, and
a mixed layer comprising, metal ions selected from the group consisting of silver ions, copper ions and zinc ions, and metal in a metal state, said mixed layer being fixed on said photocatalyst layer.

11. An antimicrobial solid material which comprises a substrate, a deep-layer antimicrobial metal ion layer supported on the substrate, an ion release-suppressing layer containing an antimicrobial metal in a metal state fixed on said antimicrobial metal ion layer, and a surface-layer antimicrobial metal ion layer supported on said ion release-suppressing layer.

12. An antimicrobial solid material which comprises both silver ions and copper ions as antimicrobial metal ions, and both silver and copper as antimicrobial metals in a metal state.

13. An antimicrobial solid material which comprises:
a substrate,
an antimicrobial metal ion layer comprising silver ions and copper ions, said metal ion layer being fixed on said substrate, and
an ion release-suppressing layer comprising particles of photocatalyst and metal in a metal state, through which said antimicrobial metal ions fixed to part of gaps between said particles permeable, said ion release-suppressing layer being fixed on said antimicrobial metal ion layer and suppressing release of said metal ions.

14. The antimicrobial solid material according to any one of claims 1 to 6, 11 and 12, wherein said antimicrobial metal in a metal state comprises metal particles having an average particle size of 100 nm or less.

15. A process for producing an antimicrobial solid material which comprises:
an ion applying step in which metal ions selected from the group consisting of silver ions, copper ions and zinc ions, as antimicrobial metal ions, are applied on the surface of a substrate, and
a reducing step in which a portion of said antimicrobial metal ions are reduced to an antimicrobial metal in a metal state.

16. The process for producing an antimicrobial solid material according to claim 15, wherein the antimicrobial metal ions are applied to a porous substrate by absorbing the antimicrobial metal ions.

17. The process for producing an antimicrobial solid material according to claim 15, wherein said reducing step is accomplished by using a step selected from the group consisting of photoirradiation, using a sacrifice oxidizer or applying thermal treatment.

18. A process for producing an antimicrobial solid material which comprises:
   a photocatalyst layer forming step for forming a porous photocatalyst layer on the surface of a porous substrate,
   a soaking step to absorb antimicrobial metal ions to the substrate to which said photocatalyst layer is formed, and
   an irradiating step to deposit an antimicrobial metal in a metal state by irradiating light to the photocatalyst layer containing the antimicrobial metal ions.

19. A process for producing an antimicrobial solid material which comprises:
   a step of preparing an inorganic porous substrate,
   a step of forming a porous photocatalyst layer comprising $TiO_2$ on said substrate by coating a titanium oxide sol to said substrate and then baking,
   a step of dipping the substrate to which the photocatalyst layer is formed in a solution containing antimicrobial metal ions, and
   an irradiating step to deposit an antimicrobial metal in a metal state by irradiating light to the photocatalyst layer containing the antimicrobial metal ions.

20. An antimicrobial treatment method of a liquid which comprises
   placing, in a liquid to be treated, an antimicrobial solid material having a substrate, an antimicrobial metal ion layer fixed to the substrate, and an ion release-suppressing layer fixed on said antimicrobial metal ion layer and containing metal in a metal state, and
   irradiating light containing an ultraviolet ray to said antimicrobial solid material to control a released amount of antimicrobial metal ions to the liquid to be treated by controlling deposition of the metal in a metal state at the surface of the antimicrobial solid material.

21. The antimicrobial treatment method of a liquid according to claim 20, wherein said metal in a metal state is an antimicrobial metal.

22. The antimicrobial treatment method of a liquid according to claim 20, wherein a released amount of the antimicrobial metal ions in the liquid to be treated is controlled by changing the intensity of said ultraviolet ray.

23. The antimicrobial treatment method of a liquid according to any one of claims 20 to 22, wherein said antimicrobial metal ions are silver ions, copper ions or zinc ions.

24. A water treatment device which comprises a passage in which the antimicrobial solid material according to claim 1 is placed.

25. A water treatment device which comprises a passage in which the antimicrobial solid material according to claim 7 is placed.

26. A method of providing antimicrobial treatment at a drain trap or a pop-up stopper which comprises providing the antimicrobial solid material according to claim 1 to the drain trap or the pop-up stopper.

27. A method of providing antimicrobial treatment at a drain trap or a pop-up stopper which comprises providing the antimicrobial solid material according to claim 7 to the drain trap or the pop-up stopper.

28. An antimicrobial solid material which comprises:
   a layer comprising a substance having a photocatalytic function fixed on the surface of a substrate, and
   an initially effective antimicrobial agent and an enduringly effective antimicrobial agent supported on said layer.

29. An antimicrobial solid material which comprises:
   a substrate,
   a first layer, comprising an initially effective antimicrobial agent, fixed on said substrate, and
   a second layer, comprising an enduringly effective antimicrobial agent and a substance having a photoctalytic function, fixed on said first layer.

30. An antimicrobial solid material which comprises:
   a storage portion of an antimicrobial component, and
   a suppressing layer containing a photocatalytic function, which inhibits elution of the antimicrobial component from said storage portion.

31. An antimicrobial solid material which comprises:
   a substrate,
   a first layer comprising a storage portion of an antimicrobial component and a portion which inhibits elution of the antimicrobial component from said storage portion, fixed on said substrate, and
   a surface layer which releases the antimicrobial component fixed on the first layer.

32. The antimicrobial solid material according to any one of claims 3 to 8 and 10 to 11, wherein said substrate is a porous ceramic material.

33. The antimicrobial solid material according to claim 32, wherein said porous ceramic material has an open porosity of at least 55% by volume.

34. A method of providing antimicrobial treatment to a liquid, comprising the steps of:
   placing an antimicrobial solid material according to claim 7 or 8 in a liquid to be treated, and
   irradiating said antimicrobial solid material with ultraviolet light, said iradiation causing metal ions to be released into said liquid.

* * * * *